US007795206B2

(12) United States Patent
Wilks et al.

(10) Patent No.: US 7,795,206 B2
(45) Date of Patent: Sep. 14, 2010

(54) PEPTIDE THAT INHIBITS JANUS KINASE

(75) Inventors: Andrew Frederick Wilks, South Yarra (AU); Julie Atkin, Northcote (AU); Emmanuelle Fantino, Elwood (AU)

(73) Assignee: YM Biosciences Australia Pty Ltd, Melbourne, Victoria (AU)

( * ) Notice: Subject to any disclaimer, the term of this patent is extended or adjusted under 35 U.S.C. 154(b) by 385 days.

(21) Appl. No.: 11/544,834

(22) Filed: Oct. 5, 2006

(65) Prior Publication Data
US 2007/0032411 A1    Feb. 8, 2007

Related U.S. Application Data

(62) Division of application No. 10/470,957, filed as application No. PCT/AU02/00088 on Jan. 30, 2002, now abandoned.

(30) Foreign Application Priority Data
Jan. 30, 2001    (AU) .................................. PR 2791

(51) Int. Cl.
*A61K 38/00*    (2006.01)
*A61K 38/04*    (2006.01)
(52) U.S. Cl. ................................ 514/2; 514/9; 530/328
(58) Field of Classification Search ........................ None
See application file for complete search history.

(56) References Cited

U.S. PATENT DOCUMENTS

| 5,194,392 | A | * | 3/1993 | Geysen ........................ 436/518 |
| 5,556,762 | A | * | 9/1996 | Pinilla et al. .................... 506/5 |
| 5,914,393 | A | * | 6/1999 | Coleman et al. ............ 536/23.5 |
| 6,008,058 | A | * | 12/1999 | Spatola et al. .................. 506/9 |
| 6,136,595 | A |   | 10/2000 | Ihle et al. |
| 6,210,654 | B1 |   | 4/2001 | Ihle et al. |
| 6,313,129 | B1 |   | 11/2001 | Uckun et al. |
| 2004/0137518 | A1 |   | 7/2004 | Lambert et al. |

FOREIGN PATENT DOCUMENTS

| WO |   98/49188 | * 11/1998 |
| WO | WO-00/18895 |   4/2000 |

OTHER PUBLICATIONS

Branden et al., "Introduction to Protein Structure", Garland Publishing Inc., New York, 1991, p. 247.*
Udaka et al., J. Biol. Chem. 270:24130-24134, 1995.*
Pierce et al., Mol. Diversity 1:259-265, 1995.*
Gausterer et al., "In Vivo Target Validation: Methodology and Case Studies on the Janus Kinase Tyk2", Anti-Inflammatory & Anti-Allergy Agents in Medicinal Chemistry 6:29-45, 2007.*
Branden et al., "Introduction to Protein Structure Second Edition", Garland Publishing Inc., New York, 1999, pp. 374-375.*
Drenth et al., "Principles of X-ray Crystallography," Springer, New York, 1999, p. 1.*
Sudbeck et al., "Structure-based Design of Specific Inhibitors of Janus Kinase 3 as Apoptosis-inducing Antileukemic Agents", Clin. Cancer Res. 5:1569-1582, 1999.*
Branden et al., "Introduction to Protein Structure," Second Edition, Garland Publishing Inc., New York, 1999, pp. 374-375.
Drenth, "Principles of Protein X-Ray Crystallography," Springer, New York, 1999, p. 1.
Flower, "Cutting Edge Approaches," Royal Society of Chemistry, Cambridge, UK, 2002, pp. 1 and 21-27.
Lindauer et al., Protein Engineer (2001) 14:27-37.
Non-Final Office Action for U.S. Appl. No. 10/470,957, mailed on May 12, 2008.
Saharinen et al., J. Biol. Chem. (2002) 277:47954-47963.
Saharinen et al., Mol. Cell. Biol. (2000) 20:3387-3395.
Sudbeck et al., Clin. Cancer Res. (1999) 5:1569-1582.
Yeh et al., Proc. Natl. Acad. Sci. USA (2000) 97:8991-8996.
Blom et al., "Sequence- and Structure-Based Prediction of Eukaryotic Protein Phosphorylation Sites" J. Mol. Biol. 294:1351-1362 (1999).
Checovich et al., "Fluorescence Polarisation—A New Tool for Cell and Molecular Biology" Nature 375:254-265 (1995).
Gauzzi et al., "The Amino Terminal Region of Tyk2 Sustains the Level of Interferon α Receptor α, a Component of the Interferon α/β Receptor" PNAS USA 94:11839-11844 (1997).
Hanks and Quinn, "Protein Kinase Catalytic Domain Sequence Database: Identification of Conserved Features of Primary Structures and Classification of Family Members" Methods Enzymol. 200:38-62 (1991).
Hanks et al., "The Protein Kinase Family: Conserved Features and Deduced Phylogeny of the Catalytic Domains" Science 241:42-52 (1988).
Harpur et al., "JAK2, a Third Member of the JAK Family of Protein Tyrosine Kinases" Oncogene 7:1347-53 (1992).
Hubbard et al., "Crystal Structure of the Tyrosine Kinase Domain of the Human Insulin Receptor" Nature 372:746-54 (1994).
International Search Report mailed on May 16, 2000, for PCT/AU02/00088, filed on Jan. 30, 2002.
Kozma et al., "Activation of the Receptor Kinase Domain of the trk Oncogene by Recombination with Two Different Cellular Sequences" EMBO 7:147-54 (1988).
Mosimann et al., Protein: Structure, Function, and Genetics (1995) 23:301-317.
Overduin et al., "Three-Dimensional Solution Structure of the src Homology Domain of c-abl" Cell 70:697-704 (1992).
Richter et al., "Specific Contribution of Tyk2 JH Regions to the Binding and the Expression of the Inteferon-α/β Receptor Component IFNAR1" J. Biol. Chem. 273(38):24723-24729 (1998).

(Continued)

*Primary Examiner*—David J Steadman
(74) *Attorney, Agent, or Firm*—Morrison & Foerster LLP

(57) ABSTRACT

The present invention provides a method of selecting or designing a compound for the ability to regulate JAK activity. The method comprises assessing the ability of the compound to modulate the interaction of the pseudo-substrate loop (PSL) with the kinase like domain (KLD) of JAK. In addition the present invention provides compounds which inhibit JAK and methods of treatment of JAK-associated disease states.

6 Claims, 8 Drawing Sheets

OTHER PUBLICATIONS

Sadowski et al., "A Noncatalytic Domain Conserved Among Cytoplasmic Protein-Tyrosine Kinases Modifies the Kinase Function and Transforming Activity of Fujinami Sarcoma Virus P130gagfps" Mol. Cell. Biol. 6:4396-408 (1986).

Schindler et al., "Structural Mechanism for STI-571 Inhibition of Abelson Tyrosine Kinase" Science 289:1938-42 (2000).

Velazquez et al., "Distinct Domains of the Protein Tyrosine Kinase Tyk2 Required for Binding of Interferon-α/β and for Signal Transduction" J. Biol. Chem. 270(7):3327-3334 (1995).

Verderame and Varmus, "Highly Conserved Amino Acids in the SH2 and Catalytic Domains of v-src are Altered in Naturally Occurring, Transformation-Defective Alleles" Oncogene 9:175-82 (1994).

Wilks and Kurban, "Isolation and Structural Analysis of Murine c-fes cDNA Clones" Oncogene 3:289-94 (1988).

Wilks et al., "Two Novel Protein-Tyrosine Kinases, Each with a Second Phosphotransferase-Related Catalytic Domain, Define a New Class of Protein Kinase" Mol. Cell. Biol. 11:2057-65 (1991).

Yin et al., "Molecular Characterisation of Specific Interactions Between SHP-2 Phosphatase and JAK Tyrosine Kinases" J. Biol. Chem. 272(2):1032-1037 (1997).

* cited by examiner

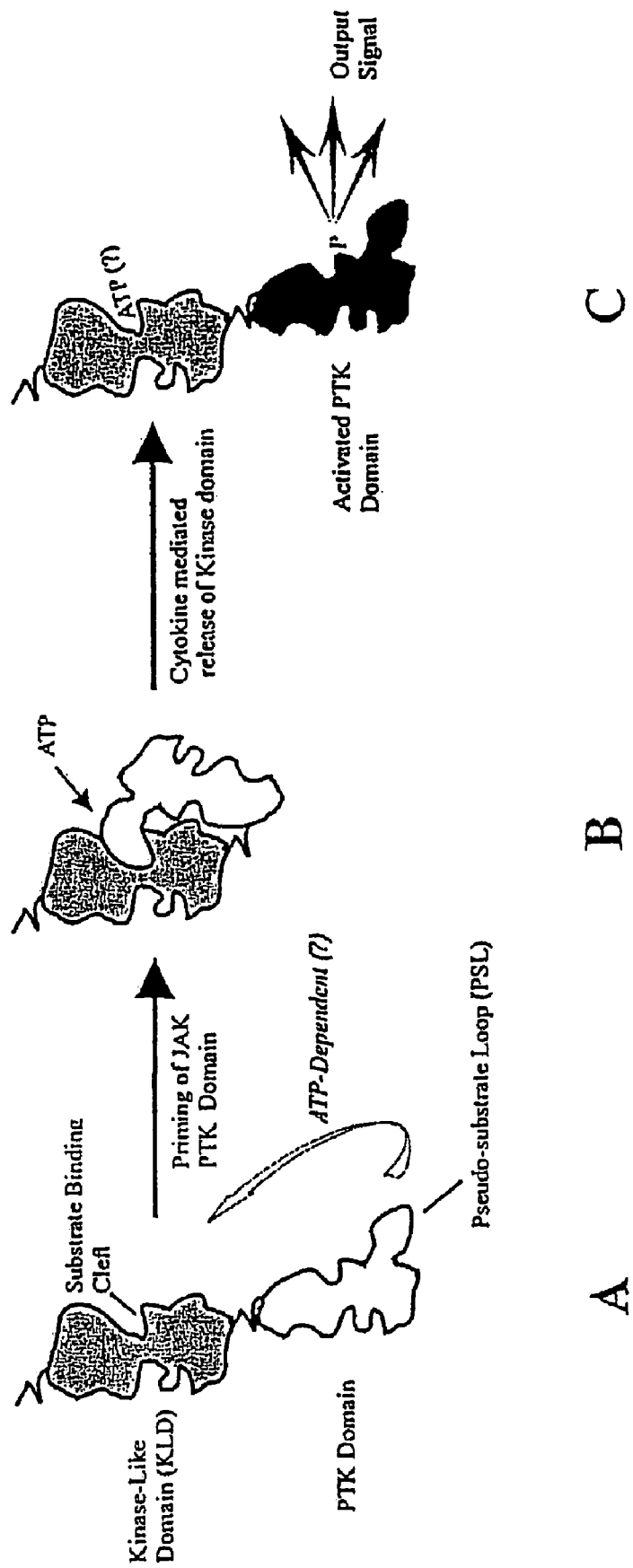
FIGURE 2: KLD-mediated Regulation of the PTK Domain of the JAK Family of PTKs

FIGURE 3a
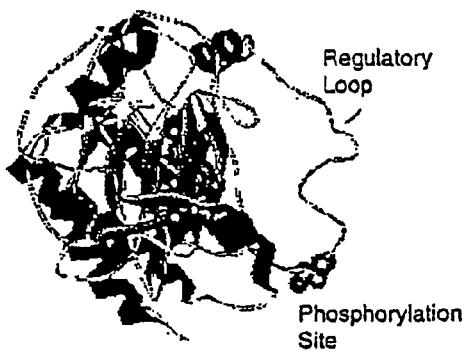
JAK2 PTK Domain (model version 1)
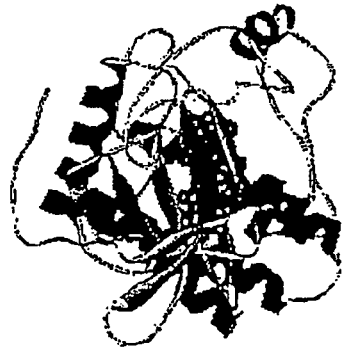
FGF Receptor PTK domain
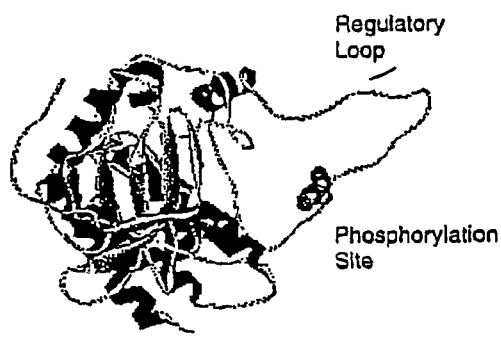
JAK2 PTK Domain (model Version 2)
HCK PTK Domain
Insulin Receptor PTK Domain
Kinase Domains: Top View

FIGURE 3b
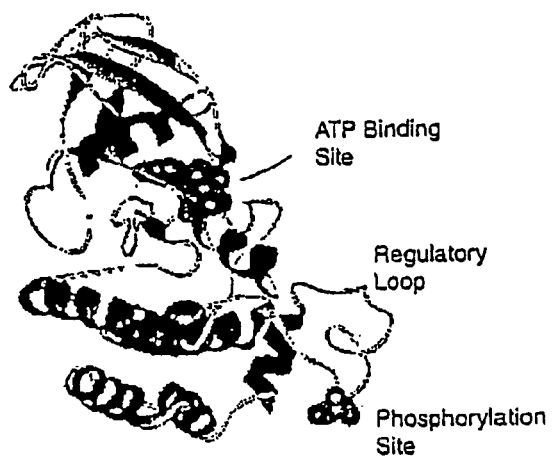
JAK2 PTK Domain (model version 1)
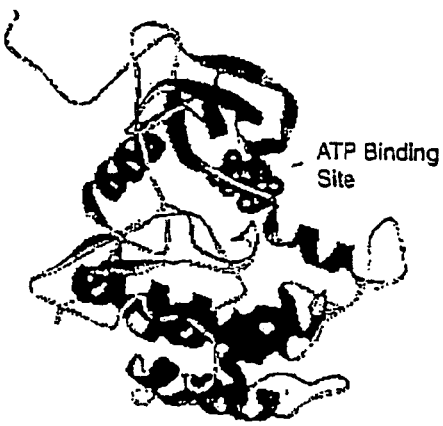
Insulin Receptor PTK Domain
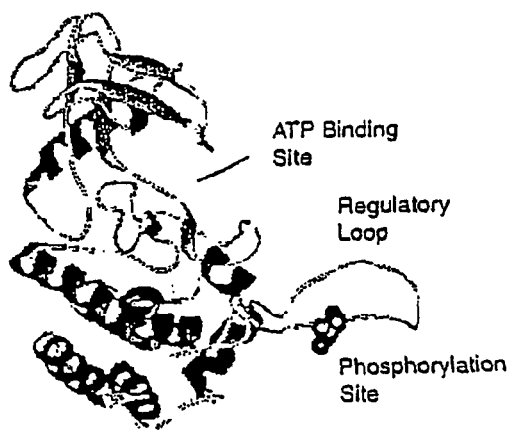
JAK2 PTK Domain (model Version 2)
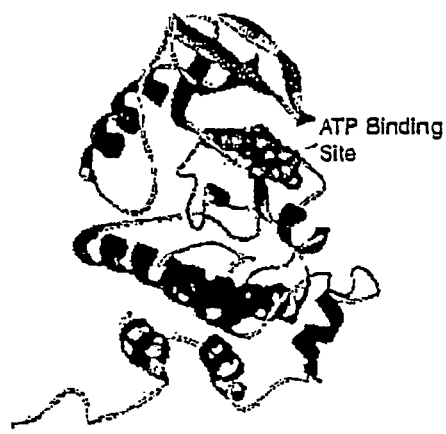
HCK PTK Domain
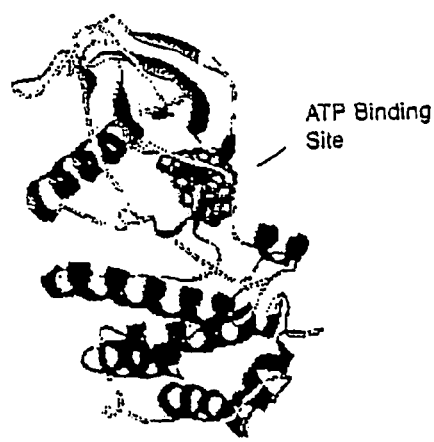
FGF Receptor PTK domain
Kinase Domains: Side View FIGURE 4: Model of the JAK2 KLD showing surface features
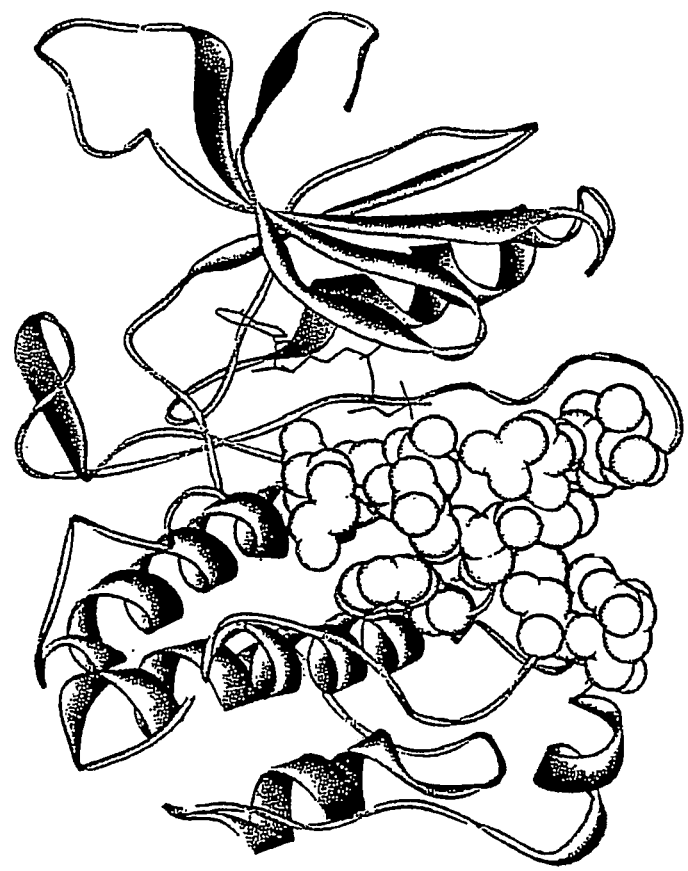

Figure 5: Ba/F3 Inhibition by PSL Peptides
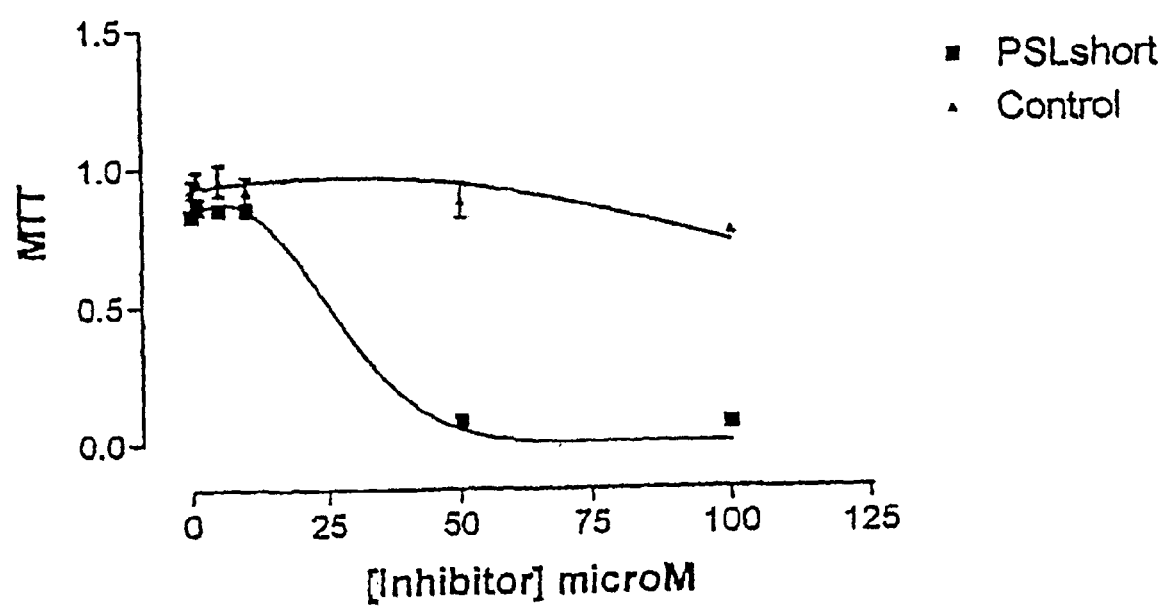

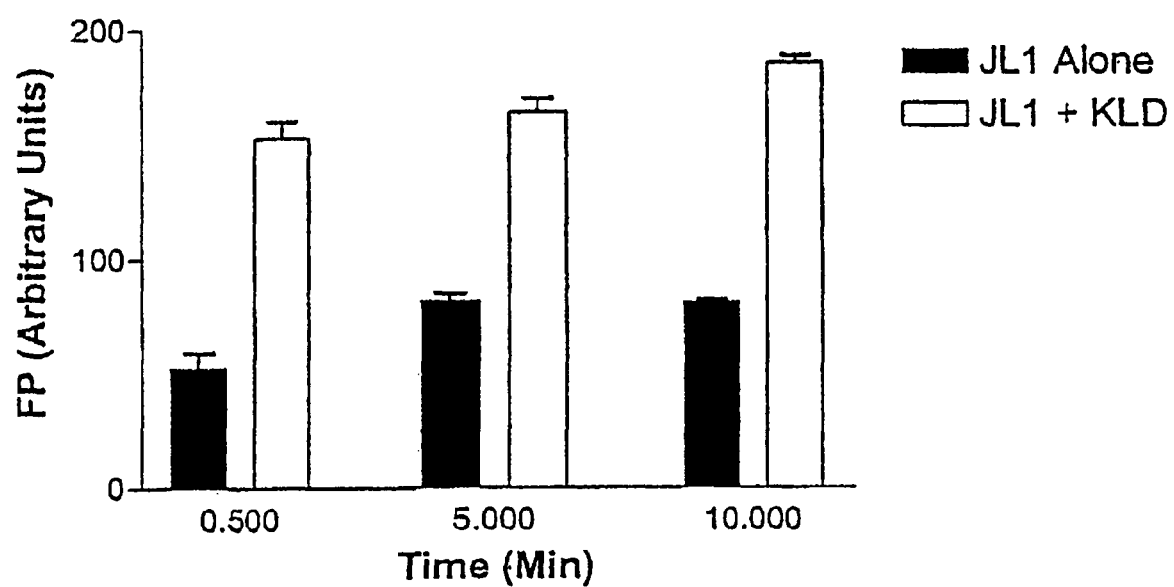
FIGURE 6a: FP Assay

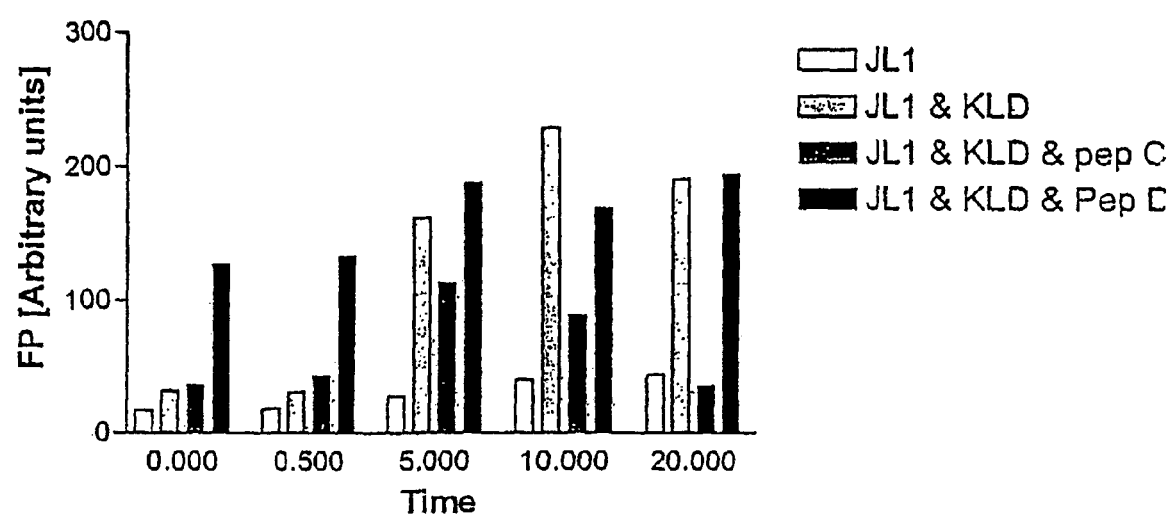
FIGURE 6b: Competition of JL1 peptide

SEQUENCE LISTING

<160> NUMBER OF SEQ ID NOS: 53

<210> SEQ ID NO 1
<211> LENGTH: 1132
<212> TYPE: PRT
<213> ORGANISM: homo sapiens

<400> SEQUENCE: 1

Met Gly Met Ala Cys Leu Thr Met Thr Glu Met Glu Gly Thr Ser Thr
1               5                   10                  15

-continued

```
Ser Ser Ile Tyr Gln Asn Gly Asp Ile Ser Gly Asn Ala Asn Ser Met
         20                  25                  30

Lys Gln Ile Asp Pro Val Leu Gln Val Tyr Leu Tyr His Ser Leu Gly
         35                  40                  45

Lys Ser Glu Ala Asp Tyr Leu Thr Phe Pro Ser Gly Glu Tyr Val Ala
 50                  55                  60

Glu Glu Ile Cys Ile Ala Ala Ser Lys Ala Cys Gly Ile Thr Pro Val
 65                  70                  75                  80

Tyr His Asn Met Phe Ala Leu Met Ser Glu Thr Glu Arg Ile Trp Tyr
                 85                  90                  95

Pro Pro Asn His Val Phe His Ile Asp Glu Ser Thr Arg His Asn Val
                100                 105                 110

Leu Tyr Arg Ile Arg Phe Tyr Phe Pro Arg Trp Tyr Cys Ser Gly Ser
             115                 120                 125

Asn Arg Ala Tyr Arg His Gly Ile Ser Arg Gly Ala Glu Ala Pro Leu
130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
            195                 200                 205

Phe Leu Pro Lys Cys Ile Arg Ala Lys Ile Gln Asp Tyr His Ile Leu
210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
            355                 360                 365

Ile Asp Gly Tyr Tyr Arg Leu Thr Ala Asp Ala His His Tyr Leu Cys
            370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
```

```
                435                 440                 445
Tyr Lys His Cys Leu Ile Thr Lys Asn Glu Asn Glu Glu Tyr Asn Leu
    450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
            485                 490                 495

Lys Cys Cys Pro Pro Lys Pro Lys Asp Lys Ser Asn Leu Leu Val Phe
                500                 505                 510

Arg Thr Asn Gly Val Ser Asp Val Pro Thr Ser Pro Thr Leu Gln Arg
        515                 520                 525

Pro Thr His Met Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
        580                 585                 590

Ser Phe Phe Glu Ala Ala Ser Met Met Ser Lys Leu Ser His Lys His
    595                 600                 605

Leu Val Leu Asn Tyr Gly Val Cys Val Cys Gly Asp Glu Asn Ile Leu
610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
        660                 665                 670

Asn Val Cys Ala Lys Asn Ile Leu Leu Ile Arg Glu Asp Arg Lys
    675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860
```

```
Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
            885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
            915                 920                 925

Met Glu Tyr Leu Pro Tyr Gly Ser Leu Arg Asp Tyr Leu Gln Lys His
            930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
            965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
            995                 1000                1005

Lys Val Lys Glu Pro Gly Glu Ser Pro Ile Phe Trp Tyr Ala Pro
1010                1015                1020

Glu Ser Leu Thr Glu Ser Lys Phe Ser Val Ala Ser Asp Val Trp
1025                1030                1035

Ser Phe Gly Val Val Leu Tyr Glu Leu Phe Thr Tyr Ile Glu Lys
1040                1045                1050

Ser Lys Ser Pro Pro Ala Glu Phe Met Arg Met Ile Gly Asn Asp
1055                1060                1065

Lys Gln Gly Gln Met Ile Val Phe His Leu Ile Glu Leu Leu Lys
1070                1075                1080

Asn Asn Gly Arg Leu Pro Arg Pro Asp Gly Cys Pro Asp Glu Ile
1085                1090                1095

Tyr Met Ile Met Thr Glu Cys Trp Asn Asn Val Asn Gln Arg
1100                1105                1110

Pro Ser Phe Arg Asp Leu Ala Leu Arg Val Asp Gln Ile Arg Asp
1115                1120                1125

Asn Met Ala Gly
    1130

<210> SEQ ID NO 2
<211> LENGTH: 13
<212> TYPE: PRT
<213> ORGANISM: homo sapiens

<400> SEQUENCE: 2

Asp Ser Pro Val Phe Trp Tyr Ala Pro Glu Cys Leu Ile
1               5                   10

<210> SEQ ID NO 3
<211> LENGTH: 13
<212> TYPE: PRT
<213> ORGANISM: homo sapiens

<400> SEQUENCE: 3

Glu Ser Pro Ile Phe Trp Tyr Ala Pro Glu Ser Leu Thr
1               5                   10

<210> SEQ ID NO 4
```

```
<211> LENGTH: 13
<212> TYPE: PRT
<213> ORGANISM: homo sapiens

<400> SEQUENCE: 4

Asp Ser Pro Val Phe Trp Tyr Ala Pro Glu Cys Leu Lys
1               5                   10

<210> SEQ ID NO 5
<211> LENGTH: 13
<212> TYPE: PRT
<213> ORGANISM: homo sapiens

<400> SEQUENCE: 5

Gln Ser Pro Ile Phe Trp Tyr Ala Pro Glu Ser Leu Ser
1               5                   10

<210> SEQ ID NO 6
<211> LENGTH: 13
<212> TYPE: PRT
<213> ORGANISM: homo sapiens

<400> SEQUENCE: 6

Lys Val Pro Ile Lys Trp Met Ala Leu Glu Ser Ile Leu
1               5                   10

<210> SEQ ID NO 7
<211> LENGTH: 13
<212> TYPE: PRT
<213> ORGANISM: homo sapiens

<400> SEQUENCE: 7

Lys Phe Pro Ile Lys Trp Thr Ala Pro Glu Ala Ala Leu
1               5                   10

<210> SEQ ID NO 8
<211> LENGTH: 11
<212> TYPE: PRT
<213> ORGANISM: homo sapiens

<400> SEQUENCE: 8

Val His Gly Asn Val Cys Thr Lys Asn Leu Leu
1               5                   10

<210> SEQ ID NO 9
<211> LENGTH: 11
<212> TYPE: PRT
<213> ORGANISM: homo sapiens

<400> SEQUENCE: 9

Ile His Gly Asn Val Cys Ala Lys Asn Ile Leu
1               5                   10

<210> SEQ ID NO 10
<211> LENGTH: 11
<212> TYPE: PRT
<213> ORGANISM: homo sapiens

<400> SEQUENCE: 10

Val His Gly Asn Val Cys Gly Arg Asn Ile Leu
1               5                   10

<210> SEQ ID NO 11
<211> LENGTH: 11
<212> TYPE: PRT
```

```
<213> ORGANISM: homo sapiens

<400> SEQUENCE: 11

Pro His Gly Asn Val Ser Ala Arg Lys Val Leu
1               5                   10

<210> SEQ ID NO 12
<211> LENGTH: 11
<212> TYPE: PRT
<213> ORGANISM: homo sapiens

<400> SEQUENCE: 12

Val His Arg Asp Leu Ala Ala Arg Asn Val Leu
1               5                   10

<210> SEQ ID NO 13
<211> LENGTH: 11
<212> TYPE: PRT
<213> ORGANISM: homo sapiens

<400> SEQUENCE: 13

Val His Arg Asp Leu Ala Ala Arg Asn Val Leu
1               5                   10

<210> SEQ ID NO 14
<211> LENGTH: 11
<212> TYPE: PRT
<213> ORGANISM: homo sapiens

<400> SEQUENCE: 14

Ile Tyr Arg Asp Leu Lys Pro Glu Asn Leu Leu
1               5                   10

<210> SEQ ID NO 15
<211> LENGTH: 8
<212> TYPE: PRT
<213> ORGANISM: homo sapiens

<400> SEQUENCE: 15

Pro Ala Glu Phe Met Arg Met Ile
1               5

<210> SEQ ID NO 16
<211> LENGTH: 15
<212> TYPE: PRT
<213> ORGANISM: homo sapiens

<400> SEQUENCE: 16

Ser Pro Ser Lys Phe Arg Met Pro Glu Ala Met Ile Gly Asn Asp
1               5                   10                  15

<210> SEQ ID NO 17
<211> LENGTH: 14
<212> TYPE: PRT
<213> ORGANISM: homo sapiens

<400> SEQUENCE: 17

Ala Tyr Ile Glu Lys Ser Lys Ser Pro Pro Ala Glu Phe Met
1               5                   10

<210> SEQ ID NO 18
<211> LENGTH: 14
<212> TYPE: PRT
```

```
<400> SEQUENCE: 18

Ala Tyr Ile Glu Lys Ser Lys Ser Pro Pro Ala Glu Phe Met
1               5                   10

<210> SEQ ID NO 19
<211> LENGTH: 27
<212> TYPE: DNA
<213> ORGANISM: homo sapiens

<400> SEQUENCE: 19
gcgcgcgaat tcacctatcc tcatatt                                     27

<210> SEQ ID NO 20
<211> LENGTH: 27
<212> TYPE: DNA
<213> ORGANISM: homo sapiens

<400> SEQUENCE: 20
gcgcgcgaat tcatcagaaa tgaagat                                     27

<210> SEQ ID NO 21
<211> LENGTH: 301
<212> TYPE: PRT
<213> ORGANISM: homo sapiens

<400> SEQUENCE: 21

Ser Glu Tyr Glu Leu Pro Glu Asp Pro Arg Trp Glu Leu Pro Arg Asp
1               5                   10                  15

Arg Leu Val Leu Gly Lys Pro Leu Gly Glu Gly Cys Phe Gly Gln Val
                20                  25                  30

Val Leu Ala Glu Ala Ile Gly Leu Asp Lys Asp Lys Pro Asn Arg Val
            35                  40                  45

Thr Lys Val Ala Val Lys Met Leu Lys Ser Asp Ala Thr Glu Lys Asp
        50                  55                  60

Leu Ser Asp Leu Ile Ser Glu Met Glu Met Met Lys Met Ile Gly Lys
65                  70                  75                  80

His Lys Asn Ile Ile Asn Leu Leu Gly Ala Cys Thr Gln Asp Gly Pro
                85                  90                  95

Leu Tyr Val Ile Val Glu Tyr Ala Ser Lys Gly Asn Leu Arg Glu Tyr
            100                 105                 110

Leu Gln Ala Arg Arg Pro Pro Gly Leu Glu Tyr Cys Tyr Asn Pro Ser
        115                 120                 125

His Asn Pro Glu Glu Gln Leu Ser Ser Lys Asp Leu Val Ser Cys Ala
130                 135                 140

Tyr Gln Val Ala Arg Gly Met Glu Tyr Leu Ala Ser Lys Lys Cys Ile
145                 150                 155                 160

His Arg Asp Leu Ala Ala Arg Asn Val Leu Val Thr Glu Asp Asn Val
                165                 170                 175

Met Lys Ile Ala Asp Phe Gly Leu Ala Arg Asp Ile His His Ile Asp
            180                 185                 190

Tyr Tyr Lys Lys Thr Thr Asn Gly Arg Leu Pro Val Lys Trp Met Ala
        195                 200                 205

Pro Glu Ala Leu Phe Asp Arg Ile Tyr Thr His Gln Ser Asp Val Trp
    210                 215                 220

Ser Phe Gly Val Leu Leu Trp Glu Ile Phe Thr Leu Gly Gly Ser Pro
225                 230                 235                 240

Tyr Pro Gly Val Pro Val Glu Glu Leu Phe Lys Leu Leu Lys Glu Gly
```

```
                    245                 250                 255
His Arg Met Asp Lys Pro Ser Asn Cys Thr Asn Glu Leu Tyr Met Met
            260                 265                 270

Met Arg Asp Cys Trp His Ala Val Pro Ser Gln Arg Pro Thr Phe Lys
        275                 280                 285

Gln Leu Val Glu Asp Leu Asp Arg Ile Val Ala Leu Thr
    290                 295                 300

<210> SEQ ID NO 22
<211> LENGTH: 306
<212> TYPE: PRT
<213> ORGANISM: homo sapiens

<400> SEQUENCE: 22

Ser Ser Val Phe Val Pro Asp Glu Trp Glu Val Ser Arg Glu Lys Ile
1               5                   10                  15

Thr Leu Leu Arg Glu Leu Gly Gln Gly Ser Phe Gly Met Val Tyr Glu
            20                  25                  30

Gly Asn Ala Arg Asp Ile Ile Lys Gly Glu Ala Glu Thr Arg Val Ala
        35                  40                  45

Val Lys Thr Val Asn Glu Ser Ala Ser Leu Arg Glu Arg Ile Glu Phe
    50                  55                  60

Leu Asn Glu Ala Ser Val Met Lys Gly Phe Thr Cys His His Val Val
65                  70                  75                  80

Arg Leu Leu Gly Val Val Ser Lys Gly Gln Pro Thr Leu Val Val Met
            85                  90                  95

Glu Leu Met Ala His Gly Asp Leu Lys Ser Tyr Leu Arg Ser Leu Arg
        100                 105                 110

Pro Glu Ala Glu Asn Asn Pro Gly Arg Pro Pro Thr Leu Gln Glu
    115                 120                 125

Met Ile Gln Met Ala Ala Glu Ile Ala Asp Gly Met Ala Tyr Leu Asn
130                 135                 140

Ala Lys Lys Phe Val His Arg Asp Leu Ala Ala Arg Asn Cys Met Val
145                 150                 155                 160

Ala His Asp Phe Thr Val Lys Ile Gly Asp Phe Gly Met Thr Arg Asp
            165                 170                 175

Ile Glu Thr Asp Arg Lys Gly Gly Lys Gly Leu Leu Pro Val Arg Trp
        180                 185                 190

Met Ala Pro Glu Ser Leu Lys Asp Gly Val Phe Thr Thr Ser Ser Asp
    195                 200                 205

Met Trp Ser Phe Gly Val Val Leu Trp Glu Ile Thr Ser Leu Ala Glu
210                 215                 220

Gln Pro Tyr Gln Gly Leu Ser Asn Glu Gln Val Leu Lys Phe Val Met
225                 230                 235                 240

Asp Gly Gly Tyr Leu Asp Gln Pro Asp Asn Cys Pro Glu Arg Val Thr
            245                 250                 255

Asp Leu Met Arg Met Cys Trp Gln Phe Asn Pro Lys Met Arg Pro Thr
        260                 265                 270

Phe Leu Glu Ile Val Asn Leu Leu Lys Asp Asp Leu His Pro Ser Phe
    275                 280                 285

Pro Glu Val Ser Phe Phe His Ser Glu Glu Asn Lys Gly Asp Tyr Met
290                 295                 300

Asn Met
305
```

<210> SEQ ID NO 23
<211> LENGTH: 274
<212> TYPE: PRT
<213> ORGANISM: homo sapiens

<400> SEQUENCE: 23

Glu Leu Pro Glu Asp Pro Arg Trp Glu Leu Pro Arg Asp Arg Leu Val
1               5                   10                  15

Leu Gly Lys Pro Leu Gly Gln Val Val Leu Ala Glu Ala Ile Gly Leu
            20                  25                  30

Pro Asn Arg Val Thr Lys Val Ala Val Lys Met Leu Lys Ser Asp Ala
        35                  40                  45

Thr Glu Lys Asp Leu Ser Asp Leu Ile Ser Glu Met Glu Met Met Lys
    50                  55                  60

Met Ile Gly Lys His Lys Asn Ile Ile Asn Leu Leu Gly Ala Cys Thr
65                  70                  75                  80

Gln Asp Gly Pro Leu Tyr Val Ile Val Glu Tyr Ala Ser Lys Gly Asn
                85                  90                  95

Leu Arg Glu Tyr Leu Gln Ala Arg Arg Pro Pro Gln Leu Ser Ser Lys
            100                 105                 110

Asp Leu Val Ser Cys Ala Tyr Gln Val Ala Arg Gly Met Glu Tyr Leu
        115                 120                 125

Ala Ser Lys Lys Cys Ile His Arg Asp Leu Ala Ala Arg Asn Val Leu
    130                 135                 140

Val Thr Glu Asp Asn Val Met Lys Ile Ala Asp Phe Gly Leu Ala Asp
145                 150                 155                 160

Ile His His Ile Asp Tyr Tyr Lys Lys Thr Asn Gly Arg Leu Pro Val
                165                 170                 175

Lys Trp Met Ala Pro Glu Ala Leu Phe Asp Arg Ile Tyr Thr His Gln
            180                 185                 190

Ser Asp Val Trp Ser Phe Gly Val Leu Leu Trp Glu Ile Phe Thr Leu
        195                 200                 205

Gly Gly Ser Pro Tyr Pro Gly Val Pro Val Glu Glu Leu Phe Lys Leu
    210                 215                 220

Leu Lys Glu Gly His Arg Met Asp Lys Pro Ser Asn Cys Thr Asn Glu
225                 230                 235                 240

Leu Tyr Met Met Met Arg Asp Cys Trp His Ala Val Pro Ser Gln Arg
                245                 250                 255

Pro Thr Phe Lys Gln Leu Val Glu Asp Leu Asp Arg Ile Val Ala Leu
            260                 265                 270

Thr Ser

<210> SEQ ID NO 24
<211> LENGTH: 263
<212> TYPE: PRT
<213> ORGANISM: homo sapiens

<400> SEQUENCE: 24

Asp Ala Trp Glu Ile Pro Arg Glu Ser Leu Arg Leu Glu Val Lys Leu
1               5                   10                  15

Gly Gln Gly Cys Phe Gly Glu Val Trp Met Gly Thr Trp Asn Gly Thr
            20                  25                  30

Thr Arg Val Ala Ile Lys Thr Leu Lys Pro Gly Thr Met Ser Pro Glu
        35                  40                  45

Ala Phe Leu Gln Glu Ala Gln Val Met Lys Lys Leu Arg His Glu Lys

-continued

```
                50                  55                  60
Leu Val Gln Leu Tyr Ala Val Val Ser Glu Pro Ile Tyr Ile Val
 65                  70                  75                  80

Thr Glu Tyr Met Ser Lys Gly Ser Leu Leu Asp Phe Leu Lys Gly Glu
                 85                  90                  95

Thr Gly Lys Tyr Leu Arg Leu Pro Gln Leu Val Asp Met Ala Ala Gln
            100                 105                 110

Ile Ala Ser Gly Met Ala Tyr Val Glu Arg Met Asn Tyr Val His Arg
            115                 120                 125

Asp Leu Arg Ala Ala Asn Ile Leu Val Gly Glu Asn Leu Val Cys Lys
        130                 135                 140

Val Ala Asp Phe Gly Leu Ala Arg Leu Ile Glu Asp Asn Glu Tyr Thr
145                 150                 155                 160

Ala Arg Gln Gly Ala Lys Phe Pro Ile Lys Trp Thr Ala Pro Glu Ala
                165                 170                 175

Ala Leu Tyr Gly Arg Phe Thr Ile Lys Ser Asp Val Trp Ser Phe Gly
            180                 185                 190

Ile Leu Leu Thr Glu Leu Thr Thr Lys Gly Arg Val Pro Tyr Pro Gly
        195                 200                 205

Met Val Asn Arg Glu Val Leu Asp Gln Val Glu Arg Gly Tyr Arg Met
    210                 215                 220

Pro Cys Pro Pro Glu Cys Pro Glu Ser Leu His Asp Leu Met Cys Gln
225                 230                 235                 240

Cys Trp Arg Lys Glu Pro Glu Glu Arg Pro Thr Phe Glu Tyr Leu Gln
                245                 250                 255

Ala Phe Leu Glu Asp Tyr Phe
            260

<210> SEQ ID NO 25
<211> LENGTH: 295
<212> TYPE: PRT
<213> ORGANISM: homo sapiens

<400> SEQUENCE: 25

Lys Asn Gln Pro Thr Glu Val Asp Pro Thr His Phe Glu Lys Arg Phe
 1               5                  10                  15

Leu Lys Arg Ile Arg Asp Leu Gly Glu Gly His Phe Gly Lys Val Glu
                 20                  25                  30

Leu Cys Arg Tyr Asp Pro Glu Asp Asn Thr Gly Glu Gln Val Ala Val
             35                  40                  45

Lys Ser Leu Lys Pro Glu Ser Gly Gly Asn His Ile Ala Asp Leu Lys
 50                  55                  60

Lys Glu Ile Glu Ile Leu Arg Asn Leu Tyr His Glu Asn Ile Val Lys
 65                  70                  75                  80

Tyr Lys Gly Ile Cys Thr Glu Asp Gly Gly Asn Gly Ile Lys Leu Ile
                 85                  90                  95

Met Glu Phe Leu Pro Ser Gly Ser Leu Lys Glu Tyr Leu Pro Lys Asn
            100                 105                 110

Lys Asn Lys Ile Asn Leu Lys Gln Gln Leu Lys Tyr Ala Val Gln Ile
        115                 120                 125

Cys Lys Gly Met Asp Tyr Leu Gly Ser Arg Gln Tyr Val His Arg Asp
    130                 135                 140

Leu Ala Ala Arg Asn Val Leu Val Glu Ser Glu His Gln Val Lys Ile
145                 150                 155                 160
```

```
Gly Asp Phe Gly Leu Thr Lys Ala Ile Glu Thr Asp Lys Glu Tyr Tyr
                165                 170                 175

Thr Val Lys Asp Asp Arg Asp Ser Pro Val Phe Trp Tyr Ala Pro Glu
            180                 185                 190

Cys Leu Met Gln Ser Lys Phe Tyr Ile Ala Ser Asp Val Trp Ser Phe
        195                 200                 205

Gly Val Thr Leu His Glu Leu Leu Thr Tyr Cys Asp Ser Asp Ser Ser
    210                 215                 220

Pro Met Ala Leu Phe Leu Lys Met Ile Gly Pro Thr His Gly Gln Met
225                 230                 235                 240

Thr Val Thr Arg Leu Val Asn Thr Leu Lys Glu Gly Lys Arg Leu Pro
                245                 250                 255

Cys Pro Pro Asn Cys Pro Asp Glu Val Tyr Gln Leu Met Arg Lys Cys
            260                 265                 270

Trp Glu Phe Gln Pro Ser Asn Arg Thr Ser Phe Gln Asn Leu Ile Glu
        275                 280                 285

Gly Phe Glu Ala Leu Leu Lys
    290                 295

<210> SEQ ID NO 26
<211> LENGTH: 300
<212> TYPE: PRT
<213> ORGANISM: homo sapiens

<400> SEQUENCE: 26

Ser Gly Ala Phe Glu Asp Arg Asp Pro Thr Gln Phe Glu Glu Arg His
1               5                   10                  15

Leu Lys Phe Leu Gln Gln Leu Gly Lys Gly Asn Phe Gly Ser Val Glu
                20                  25                  30

Met Cys Arg Tyr Asp Pro Leu Gln Asp Asn Thr Gly Glu Val Val Ala
            35                  40                  45

Val Lys Lys Leu Gln His Ser Thr Glu Glu His Leu Arg Asp Phe Glu
    50                  55                  60

Arg Glu Ile Glu Ile Leu Lys Ser Leu Gln His Asp Asn Ile Val Lys
65                  70                  75                  80

Tyr Lys Gly Val Cys Tyr Ser Ala Gly Arg Arg Asn Leu Lys Leu Ile
                85                  90                  95

Met Glu Tyr Leu Pro Tyr Gly Ser Leu Arg Asp Tyr Leu Gln Lys His
            100                 105                 110

Lys Glu Arg Ile Asp His Ile Lys Leu Leu Gln Tyr Thr Ser Gln Ile
        115                 120                 125

Cys Lys Gly Met Glu Tyr Leu Gly Thr Lys Arg Tyr Ile His Arg Asp
    130                 135                 140

Leu Ala Thr Arg Asn Ile Leu Val Glu Asn Glu Asn Arg Val Lys Ile
145                 150                 155                 160

Gly Asp Phe Gly Leu Thr Lys Val Leu Pro Gln Asp Lys Glu Tyr Tyr
                165                 170                 175

Lys Val Lys Glu Pro Gly Glu Ser Pro Ile Phe Trp Tyr Ala Pro Glu
            180                 185                 190

Ser Leu Thr Glu Ser Lys Phe Ser Val Ala Ser Asp Val Trp Ser Phe
        195                 200                 205

Gly Val Val Leu Tyr Glu Leu Phe Thr Tyr Ile Glu Lys Ser Lys Ser
    210                 215                 220

Pro Pro Ala Glu Phe Met Arg Met Ile Gly Asn Asp Lys Gln Gly Gln
225                 230                 235                 240
```

```
Met Ile Val Phe His Leu Ile Glu Leu Leu Lys Asn Asn Gly Arg Leu
                245                 250                 255

Pro Arg Pro Asp Gly Cys Pro Asp Glu Ile Tyr Met Ile Met Thr Glu
            260                 265                 270

Cys Trp Asn Asn Val Asn Gln Arg Pro Ser Phe Arg Asp Leu Ala
        275                 280                 285

Leu Arg Val Asp Gln Ile Arg Asp Asn Met Ala Gly
    290                 295                 300

<210> SEQ ID NO 27
<211> LENGTH: 299
<212> TYPE: PRT
<213> ORGANISM: homo sapiens

<400> SEQUENCE: 27

Ala Gln Leu Tyr Ala Cys Gln Asp Pro Thr Ile Phe Glu Glu Arg His
1               5                   10                  15

Leu Lys Tyr Ile Ser Gln Leu Gly Lys Gly Asn Phe Gly Ser Val Glu
            20                  25                  30

Leu Cys Arg Tyr Asp Pro Leu Ala His Asn Thr Gly Ala Leu Val Ala
        35                  40                  45

Val Lys Gln Leu Gln His Ser Gly Pro Asp Gln Gln Arg Asp Phe Gln
50                  55                  60

Arg Glu Ile Gln Ile Leu Lys Ala Leu His Ser Asp Phe Ile Val Lys
65                  70                  75                  80

Tyr Arg Gly Val Ser Tyr Gly Pro Gly Arg Pro Glu Leu Arg Leu Val
                85                  90                  95

Met Glu Tyr Leu Pro Ser Gly Cys Leu Arg Asp Phe Leu Gln Arg His
            100                 105                 110

Arg Ala Arg Leu Asp Ala Ser Arg Leu Leu Leu Tyr Ser Ser Gln Ile
        115                 120                 125

Cys Lys Gly Met Glu Tyr Leu Gly Ser Arg Arg Cys Val His Arg Asp
130                 135                 140

Leu Ala Ala Arg Asn Ile Leu Val Glu Ser Glu Ala His Val Lys Ile
145                 150                 155                 160

Ala Asp Phe Gly Leu Ala Lys Leu Leu Pro Leu Asp Lys Asp Tyr Tyr
                165                 170                 175

Val Val Arg Glu Pro Gly Gln Ser Pro Ile Phe Trp Tyr Ala Pro Glu
            180                 185                 190

Ser Leu Ser Asp Asn Ile Phe Ser Arg Gln Ser Asp Val Trp Ser Phe
        195                 200                 205

Gly Val Val Leu Tyr Glu Leu Phe Thr Tyr Cys Asp Lys Ser Cys Ser
210                 215                 220

Pro Ser Ala Glu Phe Leu Arg Met Met Gly Cys Glu Arg Asp Val Pro
225                 230                 235                 240

Ala Leu Cys Arg Leu Leu Glu Leu Leu Glu Glu Gly Gln Arg Leu Pro
                245                 250                 255

Ala Pro Pro Ala Cys Pro Ala Glu Val His Glu Leu Met Lys Leu Cys
            260                 265                 270

Trp Ala Pro Ser Pro Gln Asp Arg Pro Ser Phe Ser Ala Leu Gly Pro
        275                 280                 285

Gln Leu Asp Met Leu Trp Ser Gly Ser Arg Gly
    290                 295
```

<210> SEQ ID NO 28
<211> LENGTH: 49
<212> TYPE: PRT
<213> ORGANISM: Homo sapiens

<400> SEQUENCE: 28

Ser Asp Val Trp Ser Phe Gly Ile Leu Leu Thr Glu Leu Thr Thr Lys
1               5                   10                  15

Gly Arg Val Pro Tyr Pro Gly Met Val Asn Arg Glu Val Leu Asp Gln
            20                  25                  30

Val Glu Arg Gly Tyr Arg Met Pro Cys Pro Pro Glu Cys Pro Glu Ser
        35                  40                  45

Leu

<210> SEQ ID NO 29
<211> LENGTH: 49
<212> TYPE: PRT
<213> ORGANISM: homo sapiens

<400> SEQUENCE: 29

Ser Asp Val Trp Ser Phe Gly Val Leu Leu Trp Glu Ile Phe Thr Leu
1               5                   10                  15

Gly Gly Ser Pro Tyr Pro Gly Val Pro Val Glu Glu Leu Phe Lys Leu
            20                  25                  30

Leu Lys Glu Gly His Arg Met Asp Lys Pro Ser Asn Cys Thr Asn Glu
        35                  40                  45

Leu

<210> SEQ ID NO 30
<211> LENGTH: 63
<212> TYPE: PRT
<213> ORGANISM: homo sapiens

<400> SEQUENCE: 30

Ser Asp Val Trp Ser Phe Gly Val Thr Leu His Glu Leu Leu Thr Tyr
1               5                   10                  15

Cys Asp Ser Asp Ser Ser Pro Met Ala Leu Phe Leu Lys Met Ile Gly
            20                  25                  30

Pro Thr His Gly Gln Met Thr Val Thr Arg Leu Val Asn Thr Leu Lys
        35                  40                  45

Glu Gly Lys Arg Leu Pro Cys Pro Pro Asn Cys Pro Asp Glu Val
    50                  55                  60

<210> SEQ ID NO 31
<211> LENGTH: 64
<212> TYPE: PRT
<213> ORGANISM: homo sapiens

<400> SEQUENCE: 31

Ser Asp Val Trp Ser Phe Gly Val Val Leu Tyr Glu Leu Phe Thr Tyr
1               5                   10                  15

Ile Glu Lys Ser Lys Ser Pro Pro Ala Glu Phe Met Arg Met Ile Gly
            20                  25                  30

Asn Asp Lys Gln Gly Gln Met Ile Val Phe His Leu Ile Glu Leu Leu
        35                  40                  45

Lys Asn Asn Gly Arg Leu Pro Arg Pro Asp Gly Cys Pro Asp Glu Ile
    50                  55                  60

<210> SEQ ID NO 32

-continued

<211> LENGTH: 63
<212> TYPE: PRT
<213> ORGANISM: homo sapiens

<400> SEQUENCE: 32

Ser Asp Val Trp Ser Phe Gly Val Val Leu Tyr Glu Leu Phe Thr Tyr
1               5                   10                  15

Cys Asp Lys Ser Cys Ser Pro Ser Ala Glu Phe Leu Arg Met Met Gly
                20                  25                  30

Cys Glu Arg Asp Val Pro Ala Leu Cys Arg Leu Leu Glu Leu Leu Glu
            35                  40                  45

Glu Gly Gln Arg Leu Pro Ala Pro Pro Ala Cys Pro Ala Glu Val
        50                  55                  60

<210> SEQ ID NO 33
<211> LENGTH: 57
<212> TYPE: PRT
<213> ORGANISM: homo sapiens

<400> SEQUENCE: 33

Ser Asp Val Trp Ser Phe Gly Val Thr Leu Tyr Glu Leu Leu Thr His
1               5                   10                  15

Cys Asp Ser Ser Gln Ser Pro Pro Thr Lys Phe Leu Glu Leu Ile Gly
                20                  25                  30

Ile Ala Gln Gly Gln Met Thr Val Leu Arg Leu Thr Glu Leu Leu Glu
            35                  40                  45

Arg Gly Glu Arg Leu Pro Arg Pro Asp
        50                  55

<210> SEQ ID NO 34
<211> LENGTH: 50
<212> TYPE: PRT
<213> ORGANISM: mouse

<400> SEQUENCE: 34

Ser Asp Val Trp Ser Phe Gly Val Thr Leu His Glu Leu Leu Thr Tyr
1               5                   10                  15

Cys Asp Ser Asp Phe Ser Pro Met Ala Leu Phe Leu Lys Met Ile Gly
                20                  25                  30

Pro Thr His Gly Gln Met Thr Val Thr Arg Leu Val Lys Thr Leu Lys
            35                  40                  45

Glu Gly
    50

<210> SEQ ID NO 35
<211> LENGTH: 66
<212> TYPE: PRT
<213> ORGANISM: mouse

<400> SEQUENCE: 35

Ser Asp Val Trp Ser Phe Gly Val Val Leu Tyr Glu Leu Phe Thr Tyr
1               5                   10                  15

Ile Glu Lys Ser Lys Ser Pro Val Glu Phe Met Arg Met Ile Gly
                20                  25                  30

Asn Asp Lys Gln Gly Gln Met Ile Val Phe His Leu Ile Glu Leu Leu
            35                  40                  45

Lys Ser Asn Gly Arg Leu Pro Arg Pro Glu Gly Cys Pro Asp Glu Ile
        50                  55                  60

Tyr Val

<210> SEQ ID NO 36
<211> LENGTH: 48
<212> TYPE: PRT
<213> ORGANISM: mouse

<400> SEQUENCE: 36

Ser Asp Val Trp Ser Phe Gly Val Val Leu Tyr Glu Leu Phe Thr Tyr
1               5                   10                  15

Cys Asp Lys Ser Cys Ser Pro Ser Ala Glu Phe Leu Arg Met Met Gly
                20                  25                  30

Pro Glu Arg Glu Gly Pro Pro Leu Cys Arg Leu Leu Glu Leu Leu Ala
            35                  40                  45

<210> SEQ ID NO 37
<211> LENGTH: 66
<212> TYPE: PRT
<213> ORGANISM: Rat

<400> SEQUENCE: 37

Ser Asp Val Trp Ser Phe Gly Val Val Leu Tyr Glu Leu Phe Thr Tyr
1               5                   10                  15

Ile Glu Lys Ser Lys Ser Pro Val Glu Phe Met Arg Met Ile Gly
                20                  25                  30

Asn Asp Lys Gln Gly Gln Met Ile Val Phe His Leu Ile Glu Leu Leu
            35                  40                  45

Lys Asn Asn Gly Arg Leu Pro Arg Pro Glu Gly Cys Pro Asp Glu Ile
    50                  55                  60

Tyr Val
65

<210> SEQ ID NO 38
<211> LENGTH: 57
<212> TYPE: PRT
<213> ORGANISM: Rat

<400> SEQUENCE: 38

Ser Asp Val Trp Ser Phe Gly Val Val Leu Tyr Glu Leu Phe Thr Tyr
1               5                   10                  15

Ser Asp Lys Ser Cys Ser Pro Ser Thr Glu Phe Leu Arg Met Ile Gly
                20                  25                  30

Pro Glu Arg Glu Gly Ser Pro Leu Cys His Leu Leu Glu Leu Leu Ala
            35                  40                  45

Glu Gly Arg Arg Leu Pro Pro Pro Ser
    50                  55

<210> SEQ ID NO 39
<211> LENGTH: 52
<212> TYPE: PRT
<213> ORGANISM: pig

<400> SEQUENCE: 39

Ser Asp Val Trp Ser Phe Gly Val Thr Leu His Glu Leu Leu Thr Tyr
1               5                   10                  15

Cys Asp Ser Asp Ser Ser Pro Met Ala Leu Phe Leu Lys Met Ile Gly
                20                  25                  30

Pro Thr His Gly Gln Met Thr Val Thr Arg Leu Val Asn Thr Leu Lys
            35                  40                  45

```
Glu Gly Lys Arg
    50

<210> SEQ ID NO 40
<211> LENGTH: 66
<212> TYPE: PRT
<213> ORGANISM: pig

<400> SEQUENCE: 40

Ser Asp Val Trp Ser Phe Gly Val Val Leu Tyr Glu Leu Phe Thr Tyr
1               5                   10                  15

Ile Glu Lys Ser Lys Ser Pro Ala Glu Phe Met Arg Met Ile Gly
            20                  25                  30

Asn Asp Lys Gln Gly Gln Met Ile Val Phe His Leu Ile Glu Leu Leu
        35                  40                  45

Lys Asn Asn Gly Arg Leu Pro Arg Pro Asp Gly Cys Pro Asp Glu Ile
    50                  55                  60

Tyr Ile
65

<210> SEQ ID NO 41
<211> LENGTH: 55
<212> TYPE: PRT
<213> ORGANISM: Gallus gallus

<400> SEQUENCE: 41

Ser Asp Val Trp Ser Phe Gly Val Thr Leu Tyr Glu Leu Leu Thr Tyr
1               5                   10                  15

Cys Asp Ser Glu Ser Ser Pro Met Thr Glu Phe Leu Lys Met Ile Gly
            20                  25                  30

Pro Thr Gln Gly Gln Met Thr Val Ala Arg Leu Val Arg Val Leu Gln
        35                  40                  45

Glu Glu Lys Arg Leu Pro Arg
    50                  55

<210> SEQ ID NO 42
<211> LENGTH: 47
<212> TYPE: PRT
<213> ORGANISM: Tetraodon fluviatilis

<400> SEQUENCE: 42

Ser Asp Val Trp Ser Phe Gly Val Thr Leu Tyr Glu Leu Ile Thr Tyr
1               5                   10                  15

Cys Asp Ser Ser Lys Ser Pro Met Thr Cys Phe Leu Asp Met Ile Gly
            20                  25                  30

Trp Thr Gln Gly Gln Met Thr Val Met Arg Leu Val Lys Leu Leu
        35                  40                  45

<210> SEQ ID NO 43
<211> LENGTH: 60
<212> TYPE: PRT
<213> ORGANISM: Tetraodon fluviatilis

<400> SEQUENCE: 43

Ser Asp Val Trp Ser Phe Gly Val Val Leu Tyr Glu Leu Phe Thr His
1               5                   10                  15

Ser Ser Arg Asn Ser Ser Pro Pro Thr Val Phe Met Ser Met Met Gly
            20                  25                  30

Asn Asp Lys Gln Gly Gln Leu Ile Val Tyr His Leu Ile Glu Leu Leu
        35                  40                  45
```

```
Lys Ser Gly Ser Arg Leu Pro Gln Pro Leu Asp Cys
    50                  55                  60

<210> SEQ ID NO 44
<211> LENGTH: 64
<212> TYPE: PRT
<213> ORGANISM: Tetraodon fluviatilis

<400> SEQUENCE: 44

Ser Asp Val Trp Ser Phe Gly Val Val Leu Tyr Glu Leu Phe Ser Tyr
1               5                   10                  15

Cys Asp Ile Asn Ser Asn Pro Lys Arg Leu Tyr Met Gln Gln Ile Gly
                20                  25                  30

His Asn Val Gln Thr Pro Ser Ile Ser Leu His Leu Ala Asn Ile Leu
            35                  40                  45

Lys Ser Asn Trp Arg Leu Pro Ala Pro Pro Asp Cys Pro Ala Lys Val
    50                  55                  60

<210> SEQ ID NO 45
<211> LENGTH: 54
<212> TYPE: PRT
<213> ORGANISM: Tetraodon fluviatilis

<400> SEQUENCE: 45

Ser Asp Val Trp Ser Phe Gly Val Thr Leu Tyr Glu Ile Leu Thr His
1               5                   10                  15

Cys Asp Pro Lys Gln Ser Pro Arg Lys Lys Phe Glu Glu Met Leu Glu
                20                  25                  30

Pro Lys Ser Leu Ile Asn Gln Val Pro Leu Ile Glu Leu Leu Glu Lys
            35                  40                  45

Lys Met Arg Leu Pro Cys
    50

<210> SEQ ID NO 46
<211> LENGTH: 48
<212> TYPE: PRT
<213> ORGANISM: Cyprinus Carpio

<400> SEQUENCE: 46

Ser Asp Val Trp Ser Phe Gly Val Thr Met Tyr Glu Leu Leu Thr Tyr
1               5                   10                  15

Cys Asp Ile Ser Cys Ser Pro Met Ser Val Phe Leu Met Ile Gly Pro
                20                  25                  30

Thr His Gly Gln Met Thr Val Thr Arg Leu Val Lys Val Leu Glu Glu
            35                  40                  45

<210> SEQ ID NO 47
<211> LENGTH: 54
<212> TYPE: PRT
<213> ORGANISM: Cyprinus Carpio

<400> SEQUENCE: 47

Ser Asp Ile Trp Ser Phe Gly Ile Val Leu His Glu Leu Phe Ser Tyr
1               5                   10                  15

Cys Asp Ile Ser Arg Asn Pro Gln Lys Ile Val Tyr Pro Glu Asp Arg
                20                  25                  30

Lys Leu Cys Pro Glu Val Arg Pro Trp Leu Ser Ile Phe Leu Ile Phe
            35                  40                  45

Ser Lys Asp Asn Trp Arg
```

```
<210> SEQ ID NO 48
<211> LENGTH: 44
<212> TYPE: PRT
<213> ORGANISM: Danio rerio

<400> SEQUENCE: 48

Ser Asp Val Trp Ser Phe Gly Val Thr Met Tyr Glu Leu Leu Thr Tyr
1               5                   10                  15

Cys Asp Ala Ser Cys Ser Pro Met Ser Val Phe Leu Lys Leu Ile Gly
            20                  25                  30

Pro Thr His Gly Gln Met Thr Val Thr Arg Leu Val
        35                  40

<210> SEQ ID NO 49
<211> LENGTH: 50
<212> TYPE: PRT
<213> ORGANISM: Danio rerio

<400> SEQUENCE: 49

Ser Asp Val Trp Ser Phe Gly Val Val Leu Tyr Glu Leu Phe Thr Tyr
1               5                   10                  15

Ser Glu Lys Ser Cys Ser Pro Pro Ala Val Phe Met Glu Gln Met Gly
            20                  25                  30

Glu Asp Lys Gln Gly Gln Met Ile Val Tyr His Leu Ile Asp Leu Leu
        35                  40                  45

Lys Arg
    50

<210> SEQ ID NO 50
<211> LENGTH: 50
<212> TYPE: PRT
<213> ORGANISM: Danio rerio

<400> SEQUENCE: 50

Ser Asp Val Trp Ser Phe Gly Val Val Leu Tyr Glu Leu Phe Thr Tyr
1               5                   10                  15

Ser Asp Lys Leu Cys Ser Pro Pro Thr Val Phe Leu Ser Met Val Gly
            20                  25                  30

Gly Asp Lys Gln Gly Gln Thr Ile Val Tyr His Leu Ile Asp Leu Leu
        35                  40                  45

Lys Arg
    50

<210> SEQ ID NO 51
<211> LENGTH: 46
<212> TYPE: PRT
<213> ORGANISM: Drosophila melanogaster

<400> SEQUENCE: 51

Ser Asp Val Trp Ser Tyr Gly Val Thr Leu Phe Glu Met Phe Ser Arg
1               5                   10                  15

Gly Glu Glu Pro Asn Leu Val Pro Ile Gln Thr Ser Gln Glu Asp Phe
            20                  25                  30

Leu Asn Arg Leu Gln Ser Gly Glu Arg Leu Asn Arg Pro Ala
        35                  40                  45

<210> SEQ ID NO 52
<211> LENGTH: 8
```

```
<212> TYPE: PRT
<213> ORGANISM: Artificial Sequence
<220> FEATURE:
<223> OTHER INFORMATION: Chemically synthesized
<220> FEATURE:
<221> NAME/KEY: VARIANT
<222> LOCATION: 1
<223> OTHER INFORMATION: Xaa = proline or glycine
<220> FEATURE:
<221> NAME/KEY: VARIANT
<222> LOCATION: 2
<223> OTHER INFORMATION: Xaa = alanine, valine, leucine or isoleucine
<220> FEATURE:
<221> NAME/KEY: VARIANT
<222> LOCATION: 3
<223> OTHER INFORMATION: Xaa = glutamate or aspartate
<220> FEATURE:
<221> NAME/KEY: VARIANT
<222> LOCATION: 4
<223> OTHER INFORMATION: Xaa = tyrosine or phenylalanine
<220> FEATURE:
<221> NAME/KEY: VARIANT
<222> LOCATION: 5
<223> OTHER INFORMATION: Xaa = leucine, methionine or isoleucine
<220> FEATURE:
<221> NAME/KEY: VARIANT
<222> LOCATION: 6
<223> OTHER INFORMATION: Xaa = arginine or lysine
<220> FEATURE:
<221> NAME/KEY: VARIANT
<222> LOCATION: 7
<223> OTHER INFORMATION: Xaa = leucine, isoleucine or methionine
<220> FEATURE:
<221> NAME/KEY: VARIANT
<222> LOCATION: 8
<223> OTHER INFORMATION: Xaa = leucine, methionine or isoleucine

<400> SEQUENCE: 52

Xaa Xaa Xaa Xaa Xaa Xaa Xaa Xaa
1               5

<210> SEQ ID NO 53
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: VARIANT
<222> LOCATION: 1, 2, 5, 6, 13, 14
<223> OTHER INFORMATION: Xaa = any amino acid
<220> FEATURE:
<221> NAME/KEY: VARIANT
<222> LOCATION: 8
<223> OTHER INFORMATION: Xaa = leucine or methionine
<220> FEATURE:
<221> NAME/KEY: VARIANT
<222> LOCATION: 9
<223> OTHER INFORMATION: Xaa = arginine or lysine

<400> SEQUENCE: 53

Xaa Xaa Ser Pro Xaa Xaa Phe Xaa Xaa Met Ile Gly Xaa Xaa
1               5                   10
```

PEPTIDE THAT INHIBITS JANUS KINASE

CROSS-REFERENCE TO RELATED APPLICATIONS

This application is a divisional of U.S. application Ser. No. 10/470,957, filed Jan. 21, 2004 now abandoned, which is a U.S. National Phase of PCT/AU02/00088, having an international filing date of Jan. 30, 2002, which claims the benefit of Australian Application Serial No. PR 2791, filed Jan. 30, 2001. The contents of each of these documents are incorporated herein by reference in their entirety.

Reference to Sequence Listing Submitted via EFS-Web

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 415852000410Seqlist.txt | Jul.8 7, 2009 | 49,152 bytes |

FIELD OF THE INVENTION

The present invention relates to the field of regulators of the JAK family of protein tyrosine kinases. More particularly, the present invention relates to assays and screens for chemical entities which regulate the activity of the JAK family of protein tyrosine kinases. The invention further relates to the use of these chemical entities in therapeutic situations where the regulation of a protein tyrosine kinase, in particular a member of the JAK family of protein tyrosine kinases is indicated.

BACKGROUND OF THE INVENTION

Since the immune system is central to the protection of an individual from an external biological threat, diseases of the immune system are therefore a consequence of one or a combination of three problems with the immune system.

- Underproduction or suppression of the immune system (e.g. AIDS or SIDS);
- Overproduction of cells of the immune system (e.g. Leukemia or Lymphoma);
- Overproduction of the effects of the immune system (e.g. Inflammation);
- Inappropriate activation of the effects of the immune system (e.g. allergy).

Treatments of diseases of the immune system are therefore aimed at either the augmentation of immune response or the suppression of inappropriate responses. Since cytokines play a pivotal role in the regulation of the immune system, they are appropriately considered to be key targets for therapeutic intervention in immune pathologies. Similarly, the intracellular signal transduction pathways that are regulated by cytokines are potential points of therapeutic intervention in diseases that involve overproduction of cytokine signaling. The JAK family of protein tyrosine kinases (PTKs) play a central role in the cytokine dependent regulation of the proliferation and end function of several important cell types of the immune system. As such they represent excellent, well-validated targets for the purpose of drug discovery; the notion being that potent and specific inhibitors of each of the four JAK family members will provide a means of inhibiting the action of those cytokines that drive immune pathologies, such as asthma (e.g. IL-13; JAK1, JAK2), and leukemia/lymphoma (e.g. IL-2: JAK1 and JAK3).

Furthermore, certain types of cancer such as prostate cancer develop autocrine production of certain cytokines as a selectable mechanism of developing growth and/or metastatic potential. An example of this is cancer of the prostate, where IL-6 is produced by and stimulates the growth of prostate cancer cell lines such as TSU and TC3 (Spiotto M T, and Chung T D, 2000). Interestingly, levels of IL-6 are elevated in sera of patients with metastatic prostate cancer.

A great deal of literature covers the area of cytokine signaling. The present inventors have focused on the JAK/STAT pathway that is involved in the direct connection of cytokine receptor to target genes (such as cell cycle regulators (e.g. p21) and anti-apoptosis genes (such as Bcl-$X_L$)).

The JAK/STAT Pathway

The delineation of a particularly elegant signal transduction pathway downstream of the non-protein tyrosine kinase cytokine receptors has recently been achieved. In this pathway the key components are: (i) A cytokine receptor chain (or chains) such as the Interleukin-4 receptor or the Interferon γ receptor; (ii) a member (or members) of the JAK family of PTKs; (iii) a member (s) of the STAT family of transcription factors, and (iv) a sequence specific DNA element to which the activated STAT will bind.

The general principles of the JAK/STAT pathway are shown below, for the IFNγ receptor, an example of the class II cytokine receptors. Although the same basic mechanism is initiated by each family of cytokine receptors, there remain discrepancies in detail which are at present unresolved, although they presumably define the specificity of the cellular response to particular cytokines.

A review of the JAK/STAT literature offers strong support to the notion that this pathway is important for the recruitment and marshalling of the host immune response to environmental insults, such as viral and bacterial infection. This is well exemplified in Table 1 and Table 2. Information accumulated from gene knock-out experiments have underlined the importance of members of the JAK family to the intracellular signaling triggered by a number of important immune regulatory cytokines (Table 7).

The therapeutic possibilities stemming from inhibiting (or enhancing) the JAK/STAT pathway are thus largely in the sphere of immune modulation, and as such are likely to be promising drugs for the treatment of a range of pathologies in this area. In addition to the diseases listed in Tables 1 and 2, inhibitors of JAKs could be used as immunosuppressive agents for organ transplants and autoimmune diseases such as lupus, multiple sclerosis, rheumatoid arthritis, Type I diabetes, autoimmune thyroid disorders, Alzheimer's disease and other autoimmune diseases. Additionally, treatment of cancers such as prostate cancer by JAK inhibitors is indicated.

TABLE 1

| Disease Type | Cell Types Involved | Characteristics |
|---|---|---|
| Atopy | | |
| Allergic Asthma | (Mast Cells) | T-cell activation of |
| Atopic Dermatitis | (Eosinophils | B-cells followed by |
| (Eczema) | (T-Cells | IgE mediated activation |
| Allergic Rhinitis | (B-Cells | of resident Mast cells and Eosinophils |

TABLE 1-continued

| Disease Type | Cell Types Involved | Characteristics |
|---|---|---|
| Cell Mediated Hypersensitivity | | |
| Allergic Contact Dermatitis | (T-cells | T-cell hypersensitivity |
| Hypersensitivity Pneumonitis | (B-cells | |
| Rheumatic Diseases | | |
| Systemic Lupus Erythematosus (SLE) | | |
| Rheumatoid Arthritis | (Monocytes) | Cytokine Production |
| Juvenile Arthritis | (Macrophages | (e.g. TNF, IL-1, |
| Sjögren's Syndrome | (Neutrophils | CSF-1, GM-CSF) |
| Scleroderma | (Mast Cells | T-cell Activation |
| Polymyositis | (Eosinophils | JAK/STAT activation |
| Ankylosing Spondylitis | (T-Cells | |
| Psoriatic Arthritis | (B-Cells | |
| Viral Diseases | | |
| Epstein Barr Virus (EBV) | Lymphocytes | JACK/STAT Activation |
| Hepatitis B | Hepatocytes | JACK/STAT Activation |
| Hepatitis C | Hepatocytes | JACK/STAT Inhibition |
| HIV | Lymphocytes | JACK/STAT Activation |
| HTLV 1 | Lymphocytes | JACK/STAT Activation |
| Varicella-Zoster Virus (VZV) | Fibroblasts | JACK/STAT Inhibition |
| Human Papilloma Virus (HPV) | Epithelial cells | JACK/STAT Inhibition |
| Cancer | | |
| Leukemia | Leucocytes | (Cytokine production |
| Lymphoma | Lymphocytes | (JAK/STAT Activation |

There are many different types of protein kinase. Each type has the ability to add a phosphate group to an amino acid in a target protein. The phosphate is provided by hydrolyzing ATP to ADP. Typically, a protein kinase has an ATP-binding site and a catalytic domain that can bind a portion of the substrate protein. The JAK family of protein tyrosine kinases (PTKs) play a central role in the cytokine dependent regulation of the proliferation and end function of several important cell types of the immune system.

The JAK family of Protein Tyrosine Kinases (PTKs) represent excellent drug discovery targets for the following reasons:

They are proven key players in the cellular response to a number of important cytokines (from gene Knock-out and biochemical studies);

Whilst each of the JAK family members are relatively widely expressed, their PTK activity is activated only at sites where cytokine levels are relatively high, i.e. at a local site of inflammation;

They are enzymes permitting effective inhibition of signal amplification and facilitating drug design;

Therapeutic applications in which inhibitors of particular JAK kinases may be useful are outlined in Table 2 below:

TABLE 2

| Diseases Potentially Treatable By JAK-Based Drug Therapies | | | |
|---|---|---|---|
| Target Disease | Cytokine | JAK family member | Strength of Association |
| Asthma | IL-4 & IL-9 | JAK1 & JAK3 | +++ |
|  | IL-13 | JAK1 & JAK2 | +++ |
|  | IL-5 | JAK 2 | +++ |

TABLE 2-continued

| Diseases Potentially Treatable By JAK-Based Drug Therapies | | | |
|---|---|---|---|
| Target Disease | Cytokine | JAK family member | Strength of Association |
| Eczema | IL-4 | JAK1 & JAK3 | +++ |
|  | IFN-α | JAK1 & JAK2 | +++ |
| Food Allergy | IL-4 | JAK1 & JAK3 | +++ |
| Inflammatory Bowel Disease & Crohn's Disease | IL-4 | JAK1 & JAK3 | +++ |
| Leukaemia And Lymphoma | (IL-2) | JAK3, JAK1 & JAK2 | +++ |
| Cutaneous Inflammation | GM-CSF & IL-6 | JAK1 & JAK2 | +++ |
| Immune Suppression By Solid Tumour | IL-10 | JAK1 & TYK2 | +++ |
| Multiple Myeloma | IL-6 | JAK1, JAK2 & TYK 2 | +++ |

TABLE 3

| A list of Cytokines that use the JAK/STAST pathway for Signaling | | | | |
|---|---|---|---|---|
| CYTOKINE | JAK1 | JAK2 | JAK3 | TYK2 |
| IL-2, IL-4, IL-7, IL-9, IL15 (IL-13) | + | (+) | + | (+) |
| IL-13 | + | + | (+) | |
| IL-3, IL-5, GM-CSF | | + | | |
| IL-6, IL-11, OSM, CNTF, LIF | + | + | | + |
| IL-12 | | | | |
| Leptin | | + | | |
| GH, PRL, Epo, Tpo | | + | | |
| IFNα, IFNβ, IL-10 | + | | | + |
| IFNγ | + | | | + |

A direct comparison of the four mammalian JAK family members revealed the presence of seven highly conserved domains (Harpur et al., 1992). In seeking a nomenclature for the highly conserved domains characteristic of this family of PTKs, the classification used herein was guided by the approach of Pawson and co-workers (Sadovski et al., 1986) in their treatment of the SRC homology (SH) domains. The domains have been enumerated accordingly with most C-terminal homology domain designated JAK Homology domain 1 (JH1). The next domain N-terminal to JH1 is the kinase-related domain, designated here as the JH2 domain. Because of its overall similarity to other kinase domains it is also known as the Kinase-Like Domain or KLD. Each domain is then enumerated up to the JH7 located at the N-terminus (FIG. 1 shows a schematic representation of this nomenclature). The high degree of conservation of these JAK homology (JH) domains suggests that they are each likely to play an important role in the cellular processes in which these proteins operate. However, the boundaries of the JAK homology domains are arbitrary, and may or may not define functional domains. Nonetheless, their delineation is a useful device to aid the consideration of the overall structural similarity of this class of proteins.

The PTK Domain

The feature most characteristic of the JAK family of PTKs is the possession of two kinase-related domains (JH1 and JH2/KLD) (Wilks et al., 1991). The putative PTK domain of JAK1 (JH1) contains highly conserved motifs typical of PTK domains, including the presence of a tyrosine residue at position 1022 located 11 residues C-terminal to sub-domain VII that is considered diagnostic of membership of the tyrosine-specific class of protein kinases. Alignment of the human JAK1 PTK domain (255 amino acids), with other members of the PTK class of proteins revealed homology with other functional PTKs (for example, 28% identity with c-fes (Wilks and Kurban, 1988) and 37% homology to TRK (Kozma et al., 1988). The JH1 domains of each of the JAK family members possess a interesting idiosyncrasy within the highly conserved sub-domain VIII motif (residues 1015 to 1027 in JAK2, SEQ ID NO:1) that is believed to lie close to the active site, and define substrate specificity. The phenylalanine and tyrosine residues flanking the conserved tryptophan in this motif are unique to the JAK family of PTKs (see Table 4). Aside from this element, the JH1 domains of each of the members of the JAK family are typical PTK domains.

TABLE 4

Motif VIII of the JAK family of PTKs bears a conserved tyrosine

|  | Motif VII |
|---|---|
| JAK1 | DSPVFWYAPECLI (SEQ ID NO: 2) |
| JAK2 | ESPIFWYAPESLT (SEQ ID NO: 3) |
| Tyk2 | DSPVFWYAPECLK (SEQ ID NO: 4) |
| JAK3 | QSPIFWYAPESLS (SEQ ID NO: 5) |
| EGF-R | KVPIKWMALESIL (SEQ ID NO: 6) |
| c-SRC | KFPIKWTAPEAAL (SEQ ID NO: 7) |

The Kinase-like Domain (KLD or JH2 Domain)

Based upon cladograms generated using programmes such as Pile Up, the second kinase-like domain (KLD or JH2 Domain) is clearly ancestrally related to the broader family of kinase domains, by virtue of the presence of most of the key kinase motifs defined by Hanks, Quinn and Hunter (Hanks et al., 1988; Hanks & Quinn 1991). However, in order to distinguish the KLD domain motifs from the PTK domain motifs, they have been assigned a subscript a, (e.g $I_a$, $II_a$, $III_a$ etc.) with respect to their similarity to the sub-domains described by Hanks and co-workers (Hanks et al., 1988).

The overall sequence similarity of this domain to the kinase domains of both the PTK and serine/threonine kinase families implies that this region of the protein might also function as a protein kinase. There are, however, significant differences in the sequences of key motifs within this domain which suggest that the catalytic activity of the KLD domain may be something other than serine/threonine or tyrosine phosphorylation or indeed may not be kinase related. For example, comparison of sub-domain $VI_a$ of the KLD domain with sub-domain VI of members of the PTK and Serine/Threonine families shows the replacement of a conserved acidic amino acid (aspartic acid) with a neutral amino acid (asparagine). For example,

TABLE 5

Motif VIb of the KLD of the JAK family of PTK1 bears a conserved Asparagine residue

|  |  | Motif VIb |
|---|---|---|
| JAK1 | (KLD) | VHGNVCTKNLL (SEQ ID NO: 8) |
| JAK2 | (KLD) | IHGNVCAKNIL (SEQ ID NO: 9) |
| Tyk2 | (KLD) | VHGNVCGRNIL (SEQ ID NO: 10) |
| JAK3 | (KLD) | PHGNVSARKVL (SEQ ID NO: 11) |

TABLE 5-continued

Motif VIb of the KLD of the JAK family of PTK1 bears a conserved Asparagine residue

|  |  | Motif VIb |
|---|---|---|
| JAK1 | (JH1) | VHRDLAARNVL (SEQ ID NO: 12) |
| EGF-R |  | VHRDLAARNVL (SEQ ID NO: 13) |
| cAMPkα |  | IYRDLKPENLL (SEQ ID NO: 14) |

Further, while there is conservation of sub-domain $VII_a$ with respect to the equivalent motif in the other kinase families, the normally invariant D-F-G sequence of the PTK and serine/threonine families (motif VII) is replaced by the sequence D-P-G in motif $VII_a$ of the JH2/KLD domain. The conservation of the precise sequence of sub-domain VI in the protein kinase sub-families appears to correlate with the substrate specificity of the kinase, and thus it is possible that this domain within the members of the JAK family of PTKs, may exhibit a substrate specificity other than that previously observed for other protein kinases.

A further sequence anomaly that may suggest a substrate variation lies within the putative ATP-binding site in the kinase-related domain (sub-domain $I_a$). This domain consists of the absolutely conserved -GXGXXG- in all PTKs described to date. However, in all known JAK family members, sub-domain $I_a$ is replaced with -GXGXXT-. This glycine motif has now been defined as the ATP-binding site, with the first two glycine residues thought to bend around the nucleotide with the third glycine residue forming part of this loop. Substitution of the small side chain of glycine with the slightly larger threonine residue may disrupt the ATP-specific recognition, and confer some other substrate recognition. A viral mutation of the third glycine residue to a lysine in v-SRC abolishes the transformation and catalytic activity of this oncogene (Verdaane and Varmus 1994). It is also noteworthy, that this glycine interacts sterically with the conserved phenylalanine and glycine of the sub-domain VII motif Asp-Phe-Gly in the catalytic domain of the Insulin Receptor (Hubbard et al., 1994). This conformation is involved in maintaining an open structure between the two lobes of the catalytic domain, and perhaps the altered glycine to threonine and phenylalanine to proline in KLD suggests an alternate structural requirement.

Certain other subtle differences exist in the normally consistent spacing between key motifs in KLD as compared with a PTK domain. For example, the spacing between both components of the ATP-binding site ($I_a$ and $II_a$) is different for JAK1, JAK2, JAK3 and Tyk2 when compared with the broader protein kinase family. In JAK1 this spacing contains an extra 7 amino acids, JAK2 and JAK3 an extra 3 amino acids, and Tyk2, an extra 21 amino acids. Moreover, for JAK1, JAK2, Tyk2 and JAK3, the spacing between sub-domains $VI_a$ and $VII_a$ in this region is also longer. Conversely, the distance between sub-domains $VII_a$ and $IX_a$ in JAK1, Tyk2 and JAK3 is seven amino acids shorter that the corresponding region in the JH1 domain. It is worth noting that this sub-domain in the PTK domain contains the putative autophosphorylation tyrosine residue, while in each JAK family member, this tyrosine is not present in the KLD domain. The overall structure of this domain may be expected to be somewhat different from the catalytic domains of other members of the PTK and threonine/serine kinase families.

Regulation of the PTK Activity of JAK Kinases
Role of the KLD Domain

The tandem array of kinase domain and kinase-like domain is a defining feature of all members of the JAK family of PTKs. This fact, coupled with the high degree of conservation of the primary amino acid sequence of all members of this family, suggests that the role played by the KLD in the function of the JAK family of kinases is an important and evolutionarily conserved one. The presence of amino acid substitutions in key motifs within the KLD suggest that it is unlikely that this domain is a functional protein kinase. Indeed, attempts to demonstrate kinase activity form isolated purified KLD have so far proved to be impossible (Wilks et al., 1991) and it is often alternatively referred to as a pseudokinase domain.

SUMMARY OF THE INVENTION

The present inventors have developed a novel model of JAK kinase signaling. This model provides a number of target points at which a chemical entity may regulate JAK activity.

Accordingly, in a first aspect the present invention consists in a method of selecting or designing a compound for the ability to regulate JAK activity, the method comprising assessing the ability of the compound to modulate the interaction of the pseudo-substrate loop (PSL) with the kinase like domain (KLD) of JAK.

In a second aspect the present invention consists in a method of selecting, or designing, a compound which regulates JAK activity, the method comprising
   (i) selecting or designing a compound which has a conformation and polarity such that it interacts with at least one ligand selected from the group consisting of residues 667-679, 711-726 and 757-765 of human JAK2; and
   (ii) testing the compound for the ability to interfere with the binding of the PSL with the KLD.

The numbering of residues is based on the sequence of KLD of JAK 2. It will be understood there are corresponding regions in each of the other JAK kinases. The reference to these residues is therefore intended to define the regions of the JAK kinase with which the compound interacts.

In a third aspect the present invention consists in a compound which interacts with the PSL or the KLD such as to interfere with the binding of the PSL with the KLD such that the activity of the JAK is reduced when compared to that of the JAK in the absence of the compound.

In a fourth aspect the present invention consists in a therapeutic composition comprising an agent which inhibits the ability of PSL to bind to the KLD of JAK.

In a preferred embodiment of the fourth aspect the agent is the compound of the third aspect of the present invention.

In a fifth aspect the present invention consists in a compound which regulates JAK, the compound having the same or similar physico-chemical properties to a peptide comprising following amino acid sequence:

X1-X2-X3-X4-X5-X6-X7-X8          (SEQ ID NO: 52)

in which X1 is any amino acid, preferably proline or glycine;
X2 is any amino acid, preferably alanine, valine, leucine or isoleucine;
X3 is any amino acid, preferably glutamate or aspartate;
X4 is phenylalanine or tyrosine, preferably phenylalanine;
X5 is leucine or methionine or isoleucine;
X6 is arginine or lysine;
X7 is methionine or leucine or isoleucine, preferably methionine;
X8 is isoleucine or leucine or methionine, preferably isoleucine.

In a preferred embodiment the compound has the same or similar physico-chemical properties to a peptide having the amino acid sequence PAEFMRMI (SEQ ID NO:15).

In a further preferred embodiment the compound is a peptide comprising the following amino acid sequence:

X1-X2-X3-X4-X5-X6-X7-X8          (SEQ ID NO: 52)

in which $X_1$ to X8 are as defined above.

In yet another embodiment the compound is a peptide, the peptide having the amino acid sequence PAEFMRMI (SEQ ID NO:15).

In a sixth aspect the present invention consists in a compound obtained by the method of the first or second aspect of the present invention.

In a seventh aspect the present invention consists in a ligand which specifically binds the compound of the third, fourth or sixth aspect of the present invention.

BRIEF DESCRIPTION OF FIGURES

FIG. 2. KLD-mediated Regulation of the PTK domain of members of the JAK family of PTKs: The model involves a two step triggering mechanism, involving a "priming" phase, (panel A), wherein the JAK is converted to a latent form (panel B), followed by a "triggering" phase, (panel C), wherein the latent kinase activity of the PTK domain of the JAK is unleashed, which is dependent upon the interaction of a given cytokine receptor with its cognate ligand.

FIG. 3 shows: A. Kinase Domains Top View. Top views (i.e. looking from above the smaller lobe of the PTK domain) of three PTK domains (from HCK, Fibroblast Growth Factor Receptor and Insulin Receptor) for which the crystal structures have been determined, are shown. The molecular model of the JAK2 PTK domain is shown from the same angle. Noteworthy in this view of the JAK2 PTK domain is the large loop composed of the amino acids of the PSL.

Figure 1:
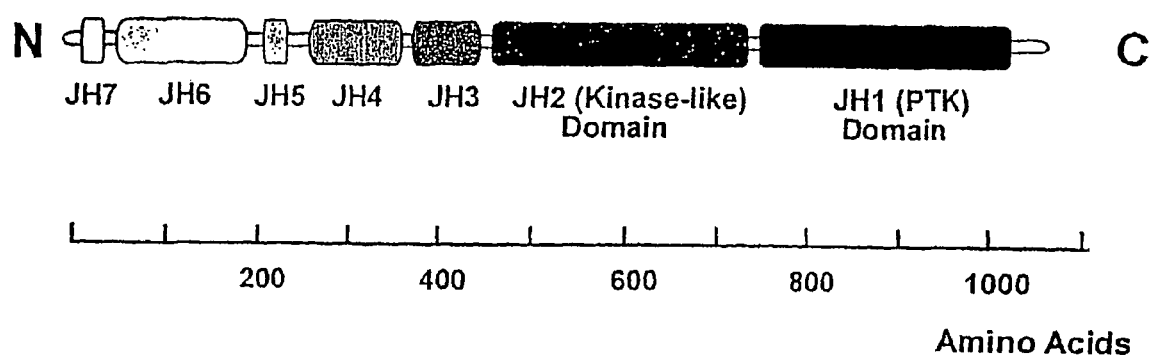
FIG. 1. Domain Structure of JAK family members: The seven JAK homology domains (JH domains) are shown as shaded boxes. JH1 is the PTK domain, whilst JH2 is the kinase-like domain, that is characteristic of this class of PTKs. The drawing is approximately to scale.

B. Kinase Domains Side View. Side views (i.e. looking from the right hand side of the PTK domain) of three PTK domains (from HCK, Fibroblast Growth Factor Receptor and Insulin Receptor) for which the crystal structures have been determined, are shown. The molecular model of the JAK2 PTK domain is shown from the same angle. Noteworthy in this view of the JAK2 PTK domain is the large loop composed of the amino acids of the PSL. The potential serine phosphorylation site in the PSL sequence has been highlighted.

FIG. 4. Model of the JAK2 KLD showing surface features: The alpha carbon chain of the KLD is shown as a ribbon structure, and the light grey patch of amino acids rendered as spheres corresponds to those amino acids analogous to those responsible for the binding of substrate peptides in the insulin receptor.

FIG. 5. Ba/F3 cell assay: Inhibition of the growth of the IL-3 dependent growth of Ba/F3 cells has been brought about by the addition of a peptide derived from JAK2 PSL. $PSL_{Short}$ PAEFMRMI (SEQ ID NO:15) and $PSL_{Control}$ SPSKFRM-PEAMIGND (SEQ ID NO:16) were added at concentrations ranging from 1μM to 100 μM in phosphate buffered saline. Cell number after three days was measured by an MTT assay.

FIG. 6. FP assay on KLD: a. Fluorescence polarization measurements (in triplicate) were taken in presence or absence of purified KLD at 30 seconds, 5 minutes, and 10 minutes following peptide (PSL-1) addition.

b. Fluorescence polarization measurements (in triplicate) were taken in presence or absence of purified KLD at 30 seconds, 5 minutes, 10 minutes and 20 minutes following peptide (PSL-1) addition. Competitor peptides PLC and PLD were added simultaneously with the fluoresceinated PSL-1 peptide.

DETAILED DESCRIPTION OF THE INVENTION

The present inventors have developed a novel model of JAK kinase signaling. This model provides a number of target points at which a chemical entity may regulate JAK activity.

The model developed by the present inventors involves a two step triggering mechanism, involving a "priming" or "cocking" phase, wherein the JAK is converted to a latent form, followed by a "triggering" phase, (wherein the latent kinase activity of the PTK domain of the JAK is unleashed), which is dependent upon the interaction of a given cytokine receptor with its cognate ligand. See FIG. 2 for details.

Phase 1: Priming

The JAK molecule is synthesized in an open conformation (FIG. 2 panel A), and is converted to a primed or cocked conformation, perhaps by the agency of a Ser/Thr kinase or phosphatase. This cocking mechanism may involve ATP, either as a co-factor for the putative Ser/Thr kinase- or phosphatase-dependent enzymes involved, or as a co-factor for binding into the ATP binding site of the KLD. The PSL of the PTK domain is loaded into its docking site in the KLD, whereupon the access of ATP to the PTK domain's ATP binding site is restricted. In this form the JAK PTK domain could be described as being inactive or latent. The PSL binds into the substrate-binding site of the kinase-like domain, indicating that the PSL may be a pseudo-substrate for a pseudo-kinase domain. The cocked JAK is loaded onto the cytokine receptor either immediately (as has been described for a number of cytokine receptors) or following cytokine stimulation of a given receptor (as has been described for Growth Hormone Receptor).

Phase 2: Triggering

Following ligand mediated binding to the cytokine receptor, the PSL is released from the KLD by a mechanism that may involve a additional kinase or phosphatase, thereby releasing the latent PTK activity in the JAK kinase domain. Ultimately the activated JAK is inactivated by binding of SOCS1 to a tyrosine in the PTK domain, and the molecule is targeted to the proteosome.

The model developed by the present inventors reveals a number of points at which a compound may interact to regulate the JAK activity. For example a compound may regulate JAK activity by interacting with the JAK at the level of the PTK domain; at the level of the loading of the PSL to the KLD (the cocking mechanism); by inhibiting the release of the PSL from the KLD (the triggering mechanism); or by causing the premature or inappropriate release of the PSL from the KLD.

Accordingly, in a first aspect the present invention consists in a method of selecting or designing a compound for the ability to regulate JAK activity, the method comprising assessing the ability of the compound to modulate the interaction of the pseudo-substrate loop (PSL) with the kinase like domain (KLD) of JAK.

In a second aspect the present invention consists in a method of selecting, or designing, a compound which regulates JAK activity, the method comprising
(i) selecting or designing a compound which has a conformation and polarity such that it interacts with at least one ligand selected from the group consisting of residues 667-679, 711-726 and 757-765 of human JAK2; and
(ii) testing the compound for the ability to interfere with the binding of the PSL with the KLD.

In a preferred embodiment of the second aspect, the method comprises selecting or designing a compound which has a conformation and polarity such that it interacts with at least one, preferably at least two, more preferably at least three and most preferably at least four ligands selected from the group consisting of residues 673, 677, 711-715, 718, 724, 759 and 760 of human JAK2.

The numbering of residues is based on the sequence of KLD of JAK 2. It will be understood there are corresponding regions in each of the other JAK kinases. The reference to these residues is therefore intended to define the regions of the JAK kinase with which the compound interacts.

As will be appreciated the method of selection or design may be conducted in a number of ways. Without limiting the general applicability of the present invention the following non-limiting examples of how the screening may be conducted are provided.

By computer modeling techniques the three dimensional structure of the PSL may be approximated. In combination with knowledge of the amino acid sequence of the PSL a compound may be designed which mimics the PSL or a region thereof in respect of physical characteristics such as shape, size, charge, polarity, etc. The compound would then be tested for its ability to bind/interact with KLD, for example by protein binding studies. Assuming that the compound demonstrated the ability to interact with KLD the compound would then be tested for biological activity in a cell based, or other in vitro, assay.

The ability of a compound to interfere with the interaction between the PSL and the KLD may also occur as a result of the compound binding to or altering the conformation of the PSL. Once again this ability can be screened for by protein binding studies.

Using the methods of the present invention the inventors have developed compounds which regulate JAK activity.

In a third aspect the present invention consists in a compound which interacts with the PSL or the KLD such as to interfere with the binding of the PSL with the KLD such that the activity of the JAK is reduced when compared to that of the JAK in the absence of the compound.

In a preferred embodiment of the third aspect, the compound binds to the substrate-binding cleft of the KLD such as to interfere with or prevent the binding of the PSL to the KLD.

In a further preferred embodiment of the third aspect, the compound has a conformation and polarity such that it binds to at least one ligand selected from the group consisting of residues 667-679, 711-726 and 757-765 of human JAK2.

In a still further preferred embodiment of the third aspect, the compound binds to at least one, preferably at least two, more preferably at least three and most preferably at least four ligands selected from the group consisting of residues 673, 677, 711-715, 718, 723-724, 759 and 760 of human JAK2.

In another preferred embodiment the compound is composed at least in part of amino acids. It is preferred that the amino acids are derived from the sequence of the PSL. By "derived from" it is intended that the residues from the PSL which bind to the selected ligands in the compound are in the same spatial configuration as they are in the PSL. For example, the compound may comprise three residues from PSL where the residues are spaced apart by other amino acid residues or spacer groups such that the three residues are arranged spatially in the same conformation as in the PSL. As will be recognized this is analogous to the concept of conformational epitopes.

The amino acids may be D or L amino acids. Where the compound is a peptide it is preferred that the peptide is cyclic.

In a fourth aspect the present invention consists in a therapeutic composition comprising an agent which inhibits the ability of PSL to bind to the KLD of JAK.

In a preferred embodiment of the fourth aspect the agent is the compound of the third aspect of the present invention.

In a fifth aspect the present invention consists in a compound which regulates JAK, the compound having the same or similar physico-chemical properties to a peptide comprising following amino acid sequence:

X1-X2-X3-X4-X5-X6-X7-X8        (SEQ ID NO: 52)

in which X1 is any amino acid, preferably proline or glycine;
X2 is any amino acid, preferably alanine, valine, leucine or isoleucine;
X3 is any amino acid, preferably glutamate or aspartate;
X4 is phenylalanine or tyrosine, preferably phenylalanine;
X5 is leucine or methionine or isoleucine;
X6 is arginine or lysine;
X7 is methionine or leucine or isoleucine, preferably methionine;
X8 is isoleucine or leucine or methionine, preferably isoleucine.

In a preferred embodiment the compound has the same or similar physico-chemical properties to a peptide having the amino acid sequence PAEFMRMI (SEQ ID NO:15).

In a further preferred embodiment the compound is a peptide comprising the following amino acid sequence:

X1-X2-X3-X4-X5-X6-X7-X8        (SEQ ID NO: 52)

in which X1 to X8 are as defined above.

In yet another embodiment the compound is a peptide, the peptide having the amino acid sequence PAEFMRMI (SEQ ID NO:15). In a sixth aspect the present invention consists in a compound obtained by the method of the first or second aspect of the present invention.

In a seventh aspect the present invention consists in a ligand which specifically binds the compound of the third, fourth or sixth aspect of the present invention.

As will be readily understood by persons skilled in this field the methods of the present invention provide a rational method for designing and selecting compounds which interact with JAK. In the majority of cases these compounds will require further development in order to increase activity. Such further development is routine in this field and will be assisted by the information and screening methods provided in this application. It is intended that in particular embodiments the methods of the present invention includes such further developmental steps.

Accordingly, in another aspect the present invention consists in a method of designing or selecting a compound which modulates JAK activity, the method comprising subjecting a compound obtained by a method according to any one of the previous aspects of the present invention to biological screens and assessing the ability of the compound to modulate JAK activity.

In a further aspect the present invention consists in a method of treating a subject suffering from a JAK-associated disease state, the method comprising administering to the subject a compound of the present invention.

It is preferred that the JAK-associated disease state is selected from the group consisting of Asthma, Eczema, Food Allergy, Inflammatory Bowel Disease, Crohn's Disease, Leukaemia, Lymphoma, Cutaneous Inflammation, Immune Suppression By Solid Tumour and Prostate Cancer.

As used herein the term "JAK", "JAK kinase" or "JAK family" refers to protein tyrosine kinases which possess the characterizing features of JAK1, JAK2, JAK3 and TYK as described herein.

As used herein the term "JAK-associated disease state" refers to those disorders which result from aberrant JAK activity, and/or which are alleviated by inhibition of one or more of these enzymes.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will now be described with references to the following non-limiting examples.

A Model for the Priming and Activation of the JAK Family of PTKS.

Modeling the JH 1 Domain

No crystal structure of a JAK family kinase domain has so far been produced. However, the kinase domains of a number of protein tyrosine kinases and serine/threonine kinases have been crystallized (e.g. Hubbard et al., 1994; Overduin M, et al. (1992); Schindler, et al., 2000; inter alia). Using the coordinate of JAK structures it has been possible to generate a model of the human JAK2 kinase domain.

Using PsiBlast (sequence similarity search), PRO-CERYON™ and GENETHREADER™ (both threading algorithms) the protein structure database (PDB) was searched for the template most similar to the human Jak2 kinase domain. The FGF receptor kinase, insulin and SRC receptor kinase were found to be the most similar sequences available. In particular the FGFR kinase (FGFRK) was found to have a sequence identity greater 30-35%, which is high enough to create reliable models.

The sequence alignments show a sequence id (similarity) between FGFRK and Jak2K of 35% (46%). The region between 1050-1071 of human JAK2 (SEQ ID NO:1) is a long loop insert, which could not be aligned properly with any loops in the templates. The conformation and structure of this insert therefore could not be predicted reliably. This insert, however, did not interact with the ATP binding site and should not influence the reliability of the model in the vicinity of the ATP binding site.

Structural Conservation

The templates were overlaid to investigate the structural conservation of the N- and C-terminal domains of the kinase fold. While the overall fold appeared well conserved, there were some larger deviations, in particular in loop regions and the orientation of the N- and C-terminal regions. The structure of the ATP binding site was well conserved, however, smaller deviations in ligand orientations and side chain conformations can be observed.

Homology Modelling

JAK2 Protein Tyrosine Kinase Domain

Homology models were created based on the sequence alignments using Andrej Sali's Modeller program, however, initially, only the AGW FGFRK was used as template because of the above mentioned deviations in the kinase fold. Although AGW contains an inhibitor, the ligand was not modeled at this point. The AGW inhibitor shows a rather different binding mode to other more ATP-like analogues and we did not want to bias the binding site for a particular class of inhibitors too much. Homology models and sequences alignments were iteratively refined during the modelling process in 6 steps. In each step 200 models were created (based on the particular alignment) and evaluated. The sequence alignment was modified according to the evaluation. In a last step, using the sequence alignment (Table 6), a model with an ATP analogue based on the AGW and SRC templates were created. All together, 1400 models were created with Modeller and evaluated. It should be noted here that the conformation of the loop residue number 1050-1071 was extremely difficult to predict given the lack of a template in this area and the length of the loop.

Model Evaluation

Models were evaluated using the internal Modeller energy and the PROSAII™ and PROFILES3D™ evaluation procedures of six final models were selected (3 based on AGW alone, 3 based on AGW and SRC) in order to show the range of possible side chain and backbone modifications. Models based only on AGW show a better quality (average PROSAII™ score:-8.14) than the models created with two templates (average score-7.73), but both classes of models seem to result in reasonable protein structures. As expected the overall structure and fold is very similar in all models, however, uncertainties are observed in side conformations.

The Pseudosubstrate Loop

Whilst the JAK2 kinase domain appeared to conform in most respects to the structures of other PTKs, the loop structure located between amino acids 1050-1071 did not resemble any feature observed in any other kinase. Nonetheless, this loop was a highly conserved feature of the JAK family of PTKs (Table 7 & FIG. 3) and it most likely plays an important role in the function of the JAK kinase family.

TABLE 6

```
              *        20         *        40         *        60         *         8
AGW   :------SEYELPEDPRWELPRDRLVLGKPLGEGCFGQV-VLAEAIGLDKDKPNRVTKVAVKMLKSDATEKDLSDLISEM :
IR3   :SSVFVP--------DEWEVSREKITLLRELGQGSFGMVYEGNARDIIK---GEAETRVAVKTVNESASLRERIEFLNEA :
FGIA  :----------ELPEDPRWELPRDRLVLGKPLG-----QV-VLAEAIGL----PNRVTKVAVKMLKSDATEKDLSDLISEM :
SRC   :--------------DAWEIPRESLRLEVKLGQGCFGEV-WMGTW--------NGTTRVAIKTLKP-GTM-SPEAFLQEA :
j1h   :------KNQPTEVDP-THFEKRFLKRIRDLGEGHFGKV-ELCRYDPEDN----TGEQVAVKSLKPESGGNHIADLKKEI :
j2h   :------SGAFEDRDP-TQFEERHLKFLQQLGKGNFGSV-EMCRYDPLQD---NTGEVVAVKKL-QHSTEEHLRDFEREI :
j3h   :------AQLYACQDP-TIFEERHLKYISQLGKGNFGSV-ELCRYDPLAH---NTGALVAVKQL-QHSGPDQQRDFQREI :
                6       LG g fg  V                     VA6K  6                 E

0        *        100        *       120         *        140        *       1
AGW   :EMMKMIGKHKNIINLLGA--CTQDG--PLYVIVEYASKGNLREYLQ---------ARRPPGLEYCYNPSHNPEEQLSSK
IR3   :SVMK-GFTCHHVVRLLGV---VSKGQPTL-VVMELMAHGDLKSYLR---------SLRPE------AENNPGRPPPTLQ
FGIA  :EMMKMIGKHKNIINLLGA--CTQDG--PLYVIVEYASKGNLREYLQ---------ARRPP--------------QLSSK
SRC   :QVMK-KLRHEKLVQLYAV--V-SEE--PIYIVTEYMSKGSLLDFL-------------KGET----------GKYLRLP
j1h   :EILR-NLYHENIVKYKGI--CTEDGGNGIKLIMEFLPSGSLKEYLP---------KNKNKIN---------------LK
j2h   :EILK-SLQHDNIVKYKGV--CYSAGRRNLKLIMEFLPYGSLRDYLQ---------KHKERID---------------HI
j3h   :QILK-ALHSDFIVKYRGV--SYGPGRPELRLVMEYLPSGCLRDFLQ---------RHRARLD---------------AS
              664      66    g       g   6 66 E       G L   5L

60       *       180        *       200         *        220        *
AGW   :DLVSCAYQVARGMEYLASKKCIHRDLAARNVLVTEDNVMKIADFGLAR-DIHHIDYYKKTTNGRLPVKWMAPEALFDRI
IR3   :EMIQMAAEIADGMAYLNAKKFVHRDLAARNCMVAHDFTVKIGDFGMTRDIETD----RKGGKGLLPVRWMAPESLKDGV
FGIA  :DLVSCAYQVARGMEYLASKKCIHRDLAARNVLVTEDNVMKIADFGLA--DIHHIDYYKKT-NGRLPVKWMAPEALFDRI
SRC   :QLVDMAAQIASGMAYVERMNYVHRDLRAANILVGENLVCKVADFGLARLI--EDNEYTARQGAKFPIKWTAPEAALYGR
j1h   :QQLKYAVQICKGMDYLGSRQYVHRDLAARNVLVESEHQVKIGDFGLTKAIETDKEYYTVKDDRDSPVFWYAPECLMQSK
j2h   :KLLQYTSQICKGMEYLGTKRYIHRDLATRNILVENENRVKIGDFGLTKVLPQDKEYYKVKEPGESPIFWYAPESLTESK
j3h   :RLLLYSSQICKGMEYLGSRRCVHRDLAARNILVESEAHVKIADFGLAKLLPLDKDYYVVREPGQSPIFWYAPESLSDNI
              6    26   GM Y6   6HRDLaarN 6V     K6 DFG6            y        P6 W APE 1

240        *       260         *        280        *       300         *
AGW   :YTHQSDVWSFGVLLWEIFT----------------------LGGSPYPGVPVEELFKLLKEGHRMDKPSNCTNEL
IR3   :FTTSSDMWSFGVVLWE------------------------ITSLAEQPYQGLSNEQVLKFVMDGGYLDQPDNCPERV
FGIA  :YTHQSDVWSFGVLLWEIFT----------------------LGGSPYPGVPVEELFKLLKEGHRMDKPSNCTNEL
SRC   :FTIKSDVWSFGILLTELTT----------------------KGRVPYPGMVNREVLDQVERGYRMPCPPECPESL
j1h   :FYIASDVWSFGVTLHELLTYCDSDSSPM-ALFLKMIG-PTHG----------QMTVTRLVNTLKEGKRLPCPPNCPDEV
j2h   :FSVASDVWSFGVVLYELFTYIEKSKSPP-AEFMRMIGNDKQG----------QMIVFHLIELLKNNGRLPRPDGCPDEI
j3h   :FSRQSDVWSFGVVLYELFTYCDKSCSPS-AEFLRMMGCERD----------VPALCRLLELLEEGQRLPAPPACPAEV
              5   SD6WSFG6  L  E   t                          6    6   g r6   P  C   6

320         *       340        *       360         *
AGW   :YMMMRDCWHAVPSQRPTFKQLVEDLDRIVALT---------------------SEQ ID NO 21
IR3   :TDLMRMCWQFNPKMRPTFLEIVNLLKDDLHPSFPEVSFFHSEENK-GDYMNM---SEQ ID NO 22
FGIA  :YMMMRDCWHAVPSQRPTFKQLVEDLDRIVALTS--------------------SEQ ID NO 23
SRC   :HDLMCQCWRKEPEERPTFEYLQAFLEDYF------------------------SEQ ID NO 24
```

TABLE 6-continued

```
j1h  :YQLMRKCWEFQPSNRTSFQNLIEGFEALLK------------------------SEQ ID NO 25
j2h  :YMIMTECWNNNVNQRPSFRDLALRVDQIRDNMAG----------------------SEQ ID NO 26
j3h  :HELMKLCWAPSPQDRPSFSALGPQLDMLWSGSRG----------------------SEQ ID NO 27
        6M   CW   p  Rp3F  6
```

TABLE 7

| | Kinase Motif IX | Pseudosubstrate Loop | Kinase Motif X | |
|---|---|---|---|---|
| HumSRC | SDVWSFGILLTELTT---KGRVPYPG----------------MVNREVLDQVERGYRMPCPPECPESL | | | SEQ ID NO 28 |
| HumFGFR | SDVWSFGVLLWEIFT---LGGSPYPG----------------VPVEELFKLLKEGHRMDKPSNCTNEL | | | SEQ ID NO 29 |
| HwnJAK1 | SDVWSFGVTLHELLTYCDSDSSPMALFLKMIGPTH----GQMTVTRLVNTLKE--GKRLPCPPNCPDEV | | | SEQ ID NO 30 |
| HumJAK2 | SDVWSFGVVLYELFTYIEKSKSPPAEFMRMIGNDK---QGQMIVFHLIELLKNN--GRLPRPDGCPDEI | | | SEQ ID NO 31 |
| HumJAK3 | SDVWSFGVVLYELFTYCDKSCSPSAEFLRMMGCER---DVPALC-RLLELLEE--GQRLPAPPACPAEV | | | SEQ ID NO 32 |
| HumTYK2 | SDVWSFGVTLYELLTHCDSSQSPPTKFLELIGIA----QGQMTVLRLTELLER--GERLPRPD | | | SEQ ID NO 33 |
| MusJAK1 | SDVWSFGVTLHELLTYCDSDFSPMALFLKMIGPT----HGQMTVTRLVKTLKEG | | | SEQ ID NO 34 |
| MusJAK2 | SDVWSFGVVLYELFTYIEKSKSPPVEFMRMIGND---KQGQMIVFHLIELLKS--NGRLPRPEGCPDEIYV | | | SEQ ID NO 35 |
| MusJAK3 | SDVWSFGVVLYELFTYCDKSCSPSAEFLRMMGPE---------------------REGPPLCRLLELLA | | | SEQ ID NO 36 |
| RatJAK2 | SDVWSFGVVLYELFTYIEKSKSPPVEFMRMIGND---KQGQMIVFHLIELLKNNGRLPRPEGCPDEIYV | | | SEQ ID NO 37 |
| RatJAK3 | SDVWSFGVVLYELFTYSDKSCSPSTEFLRMIGPE---REGSPLCHLLELLAE----GRRLPPPS | | | SEQ ID NO 38 |
| PigJAK1 | SDVWSFGVTLHELLTYCDSDSSPMALFLKMIGPT----HGQMTVTRLVNTLKEGKR | | | SEQ ID NO 39 |
| PigJAK2 | SDVWSFGVVLYELFTYIEKSKSPPAEFMRMIGND---KQGQMIVFHLIELLKNNGRLPRPDGCPDEIYI | | | SEQ ID NO 40 |
| GGJAK1 | SDVWSFGVTLYELLTYCDSESSPMTEFLKMIGPT----QGQMTVARLVRVLQEEKRLPR | | | SEQ ID NO 41 |
| PuffJAK1 | SDVWSFGVTLYELITYCDSSKSPMTCFLDMIGWT----QGQMTVMRLVKLL | | | SEQ ID NO 42 |
| PuffJAK2 | SDVWSFGVVLYELFTHSSRNSSPPTVFMSMMGND---KQGQLIVYHLIELLKSGSRLPQPLDC | | | SEQ ID NO 43 |
| PuffJAK3 | SDVWSFGVVLYELFSYCDINSNPKRLYMQQIGHN---VQTPSISLHLANILKSNWRLPAPPDCPAKV | | | SEQ ID NO 44 |
| PuffTYK2 | SDVWSFGVTLYEILTHCDPKQSPRKKFEEMLEPKSLINQVPLIELLEKKMRLPC | | | SEQ ID NO 45 |
| CCJAK1 | SDVWSFGVTMYELLTYCDISCSPMSVFL-MIGPT----HGQMTVTRLVKVLEE | | | SEQ ID NO 46 |
| CCJAK3 | SDIWSFGIVLHELFSYCDISRNPQKIVYPEDRKL----CPEVRPWLSIFLIFSKDNWR | | | SEQ ID NO 47 |
| ZDJAK1 | SDVWSFGVTMYELLTYCDASCSPMSVFLKLIGPT----HGQMTVTRLV | | | SEQ ID NO 48 |
| ZDJAK2a | SDVWSFGVVLYELFTYSEKSCSPPAVFMEQMGED---KQGQMIVYHLIDLLKR | | | SEQ ID NO 49 |
| ZDJAK2b | SDVWSFGVVLYELFTYSDKLCSPPTVFLSMVGGD---KQGQTIVYHLIDLLKR | | | SEQ ID NO 50 |
| Hopscotch | SDVWSYGVTLFEMFSRGEEPNLVPIQTSQEDFLN--RLQSGERLNRPA | | | SEQ ID NO 51 |
| Peptides used: | PAAEFMRMI PSL$_{Short}$ | | | SEQ ID NO 15 |
| | SPSKFRMPEAMIGND PSL$_{Control}$ | | | SEQ ID NO 16 |

Three properties of this loop suggest what the function of this loop might be. Firstly, the level of conservation within the family (see Table 7) suggested that it might play a role in a process that only the JAKs participate. Secondly, its location in the three dimensional model of JAK2 is directly below the ATP binding site (see FIG. 3), a feature which was important in formulating the present inventors' hypothesis. Finally, the most highly conserved amino acids with the loop indicate a glutamate adjacent to a phenylalanine residue at the centre of the loop, which could act as a pseudosubstrate loop (PSL) as outlined below.

JAK2 Kinase-Like Domain

Using PsiBlast (sequence similarity search) and the protein structure database (PDB) was searched for the template most similar to the Jak2 kinase like domain. The ABL and the SRC receptor kinase were found to be the most similar sequences available. In particular the SRC kinase was found to have a sequence identity of about 23%, which is enough to create a model. Sequences of a number of the related kinase domains JAK1, JAK2, JAK3, IGF, FGF, SRC, ABL were aligned manually after an initial alignment with the ClustalX program. The "Composer" homology modelling program (Tripos) was used to create a three-dimensional structure of the kinase-like domain. The structure was refined using molecular dynamics simulation and simulated annealing in conjunction with the Tripos suite of programs. The Whatcheck program was used to evaluate the quality of the created models during various stages of the refinement process. FIG. 4 shows a representation of the molecular model of the human JAK2 KLD, with the residues corresponding to the putative substrate binding site (by comparison with the location of the substrate-binding site of the insulin receptor PTK domain, derived from the co-crystal of the PTK domain and its substrate (Hubbard et al., 1994) shown in green).

The Model

Any model that describes the activation of the JAK family of PTKs must account for the fact that the alteration or mutation of the primary sequence of the JAK KLD can have either an inhibitory effect or a stimulatory effect, depending upon what one is measuring (e.g. kinase activity or cytokine mediated JAK activation, for example). The JAK family of kinases is proposed to have a two step triggering mechanism, involving a "priming" or "cocking" phase, wherein the JAK is converted to a latent form, followed by a "triggering" phase, (wherein the latent kinase activity of the PTK domain of the JAK is unleashed), which is dependent upon the interaction of a given cytokine receptor with its cognate ligand. See FIG. 2 for details.

Phase 1: Priming

The JAK molecule is synthesized in an open conformation (FIG. 2 panel B), and is converted to a primed or cocked conformation, perhaps by the agency of a Ser/Thr kinase or phosphatase. This cocking mechanism may involve ATP, either as a co-factor for the putative Ser/Thr kinase-or phosphatase-dependent enzymes involved, or as a co-factor for binding into the ATP binding site of the KLD. The PSL of the PTK domain is loaded into its docking site in the KLD, whereupon the access of ATP to the PTK domain's ATP binding site is restricted. In this form the JAK PTK domain could be described as being inactive or latent. The PSL may or may not bind into the substrate-binding site of the kinase like domain, indicating that the PSL may be a pseudo-substrate for a pseudo-kinase domain. The cocked JAK is loaded onto the cytokine receptor either immediately (as has been described for a number of cytokine receptors) or following cytokine stimulation of a given receptor (as has been described for Growth Hormone Receptor).

Phase 2: Triggering

Following ligand mediated binding to the cytokine receptor, the PSL is released from the KLD by a mechanism that may (or may not) involve a additional kinase or phosphatase, thereby releasing the latent PTK activity in the JAK kinase domain. Ultimately the activated JAK is inactivated by binding of SOCS1 to a tyrosine in the PTK domain, and the molecule is targeted to the proteosome.

Conclusions

This model suggests a number of possible sites of action that a potential JAK inhibitor might act to inhibit the cytokine dependent signal; namely, at the level of the PTK domain; at the level of the loading of the PSL to the KLD (the cocking mechanism); by inhibiting the release of the PSL from the KLD (the triggering mechanism); or by causing the premature or inappropriate release of the PSL from the KLD.

EXPERIMENTAL RESULTS

Peptides from the JAK Kinase Loop are Inhibitory for IL-3 Signaling

Following the generation of an alignment of the kinase domains of all of the available members of the JAK family of PTKs with the kinase domains of human c-SRC and the human FGF-receptor (Table 6 see above) revealed the presence of a JAK-family specific loop (the putative pseudo-substrate loop or PSL) between Hanks motifs IX and X. Alignment of the PSLs present in the JAKs demonstrated that the loop structures contained conserved elements, the consensus of which was:

(SEQ ID NO: 53)
X-X-S-P-p-X-X-F-$^L/_M$-$^R/_K$-M-I-G-p-X-X-

In particular the serine/proline pair (predicted to be a site of serine phosphorylation, with a high score (0.994) using NetPhos 2.0 (Blom et al., 1999)) suggested itself as a possible site of regulation.

Two peptides were constructed based upon the PSL sequence. These were:

| | | |
|---|---|---|
| $PSL_{short}$ | PAEFMRMI | SEQ ID NO: 15 |
| $PSL_{control}$ | SPSKFRMPEAMIGND | SEQ ID NO: 16 |

These peptides were tested for biological activity by means of a proliferation assay using the murine growth factor dependent hematopoietic cell line Ba/F3. On the basis of our hypothesis of the role of how the PSL region might work, we reasoned that if these peptides were to supplant the PSL from the KLD of JAK2, then the JAK PTK activity would thereby either become unregulated, resulting in a IL-3 independent growth phenotype, or the normal IL-3 dependent growth of these cells would be inhibited. The data presented in FIG. 5 demonstrated that the $PSL_{short}$ peptide was able to inhibit growth of wild-type Ba/F3 cells grown upon IL-3, whereas they were unable to inhibit the growth of Ba/F3 cells transformed to factor independence by ectopic expression of an oncogenic form of JAK2, wherein the PTK domain of JAK2 was fused to the pointed (PNT) domain of the TEL gene product. The $PSL_{short}$ peptide was therefore capable of inhibiting cells supported by the IL-3 dependent JAK/STAT pathway (i.e. using the full-length JAK2 protein) but was unable to inhibit cells supported by the expression of the TEL/JAK2 fusion (containing only the PTK domain of JAK2). We hypothesize that the activity of the $PSL_{short}$ peptide was dependent upon the presence of the JAK2 KLD, and conclude that its mode of action is by displacement of the PSL of JAK2 from the JAK2 KLD, resulting in unprimed JAK2 molecules that cannot be triggered by IL-3.

Demonstration of Binding of Peptides from the PSL to Purified Preparations of the KLD.

Our observations that small peptides derived from the PSL were able to inhibit the IL-3 mediated proliferation of Ba/F3 cells, suggested that the $PSL_{short}$ inhibited the normal cycle of priming and triggering of the JAK2 molecule by displacing the PSL of JAK2 from its binding site in the KLD. In order to demonstrate this directly we generated highly purified (>95%) KLD of JAK2 and synthesized two fluoresceinated peptides covering the PSL of JAK2, and attempted to demonstrate binding of the peptide by the KLD. The two peptides are outlined below:

(SEQ ID NO: 17)
PSL-1 Fluorescein-A-Y-I-E-K-S-K-S-P-P-A-E-F-M

Fluorescence Polarization (FP), also known as Fluorescence Anisotropy (FA), is a means of measurement of peptide protein binding (Checovich et al., 1995). A measurement of FP is a function of a particular fluoresceinated molecule's rotational relaxation time, and is empirically a measurement of the time it takes the molecule to rotate through an angle of 68.5°. The Rotational relaxation time is related to viscosity ($\eta$), absolute temperature (T), molecular volume (V) and the gas constant (R), according to the formula:

$$FP \text{ value} \propto \text{Rotational relaxation time} = \frac{3\eta V}{RT}$$

Therefore, when temperature and viscosity are both held constant the FP value is directly related to molecular volume (i.e. to molecular size). Thus a small fluoresceinated molecule such as a peptide, will have a lower FP than a larger protein such as an antibody. Binding of a smaller fluoresceinated peptide to a larger non-fluoresceinated protein will result in the appropriation of a higher FP value by the peptide. Thus binding of a peptide to a receptor can be measured by following the FP value of a fluoresceinated peptide in the presence or absence of the putative binding protein for that peptide.

The binding of the PSL to the JAK2 KLD was tested by means of an FP assay as follows. 2 pg of the peptide PSL-1 was incubated in the presence of approximately 2.5 µg of highly purified KLD. Following a brief incubation at room temperature, a series of FP measurements were taken using a BMG POLARstar. Comparisons of FP values in the presence and absence of KLD were compared over time. These data appear in FIG. 6.

Assays for the Measurement of the Inhibition for the Function of the JAK, PSL and KLD Cell-Based Assays Proliferation Assays The model that we have developed for the allosteric regulation of the protein tyrosine kinase domain of members of the JAK family by their respective KLDs suggests a number of methods by which cell-based assays and screens for inhibitors of this regulation might be brought about. In particular it would be possible to establish cell based assays by means of the use of cytokine dependent pathway screens. One example of this would be the use of a cytokine-dependent cell line such as Ba/F3 and/or FDCP-1. Each of these cell lines requires the activation of the JAK/STAT pathway by a cytokine such as interleukin-3 (IL-3) and/or GMCSF. In the case of Ba/F3, the triggering of the release of the intrinsic protein tyrosine kinase activity of the JAK2 molecule depends on the activation of the IL-3 receptor by IL-3. In turn, the priming of the JAK2 molecule by means of the docking of the PSL into the binding site of the KLD is required. Therefore, in the presence of an inhibitor of this binding, IL-3 would not be able to release the kinase activity of JAK2, since the priming step would not have taken place. Inhibitors of the binding of the PSL into the KLD would therefore be potential inhibitors of any cytokine that worked through the JAK kinases, a list of these cytokines appears below in Table 7. An example of this type of assay is shown in FIG. 5, where inhibition of the growth of the IL-3 dependent growth of Ba/F3s has been brought about by the addition of a peptide derived from the JAK2 PSL. In these experiments this peptide is able to inhibit the growth of Ba/F3 cells at a concentration of 50 µM.

Any cell line that is dependent for its continued growth and proliferation upon the presence of a cytokine has the potential for screening for inhibitors of the binding of the PSL to the KLD.

Gene Expression Assays.

The JAK/STAT pathway is responsible for the regulation of many cytokine dependent genes. Examples of such genes would include $BC1_{XL}$ and MHC Class II genes. The generation of cell lines in which the expression of an indicator gene, such as β-galactosidase or a selectable marker, such as the gene for Neomycin resistance ($Neo^R$), is regulated by an inducible promoter element is a common method by which studies of gene regulation have been undertaken. Cell lines in which indicator genes such as these were regulated by a cytokine regulated GAS element therefore offers the potential to screen for compounds which modulate this regulation, such as inhibitors of the interaction of the PSL with the JAK KLD.

In Vitro Assays Using Purified Proteins and/or Peptides.

Assays Measuring the Binding of the PTK Domain with the KLD

We have postulated that the PTK domain is regulated by its binding or otherwise with the KLD. Therefore, by measuring the enzymatic activity of the PTK domain in the presence of the KLD, an indirect measure of the binding of the PSL to the KLD can be obtained. This can be done in a standard ELISA or Fluorescence Polarisation assay, such as those that have been described elsewhere. The presence of an inhibitor of the binding of the PSL to the KLD would be revealed by an increase in PTK activity.

Assays Measuring the Binding of Portions of the PSL with Portions of the KLD

Binding of the PSL to purified KLD could be established as a sensitive high-throughput screen for inhibitors of the interaction between the PSL and the KLD. Any means by which the binding of one protein or peptide to another could be used. Two examples of this approach would be the use of a fluoresceinated or radioactively-labeled peptide representing the PSL coupled with its binding to purified KLD.

The use of a fluorescence labeled peptide should allow the development of a fluorescence-based assay such as a fluorescence polarization assay or a FRET assay. In either of these cases, the binding of the PSL to the KLD could be determined in a 96, 384 or 1536 well format as the induction of fluorescence polarization or FRET. Therefore, inhibitors that prevent the binding of the PSL to the KLD could be detected as a consequence of reduction in this signal. An example of this type of approach in shown in FIG. 6. wherein purified KLD and a fluorescent peptide representing the PSL are combined in a 96 well plate format with the result that fluorescence polarization is induced as a consequence of the binding of their mutual association.

An alternative strategy would be to use a filter-binding assay using radio-labeled peptide and purified KLD in this case high throughput format screen could easily be established.

Methods

Cloning of JAK2 Kinase-like Domain (KLD)

RNA was prepared from γ-IFN stimulated U937 cells. cDNA (20 µl) was prepared using Superscript kit (Gibco). Using an oligo dT primer provided in the kit was used to prepare the mRNA. RT-PCR was performed using the Kinase-like domain specific primers,

```
                                          (SEQ ID NO: 19)
HJ2KLF     GCG CGC GAA TTC ACC TAT CCT CAT ATT (SEQ ID NO: 20)
HJ2KLDRE   GCG CGC GAA TTC ATC AGA AAT GAA GAT
``` and standard PCR conditions. PCR products were gel-purified from a 1% TAE agarose gel using Gibco Gel Extraction kit.

PCR products were digested using EcoR1 for 2 hr at 37° C. and then gel purified as above.

The Invitrogen bacterial expression vector pBAD/gIII (2.5 µg) was digested with EcoRI for 2 hr at 37° C. and then treated with Calf Intestinal Phosphatase for 1 hr at 37° C. After the addition of 2 µl 0.5M EDTA at 70° C. for 10 mins, the vector was applied to a PCR purification column and eluted in 50 µl TE. Vector was ligated to 10 µl PCR product using T4 ligase at 14° C. overnight. The ligation mix was transformed into competent One Shot *E. Coli.* (Invitrogen).

Sequencing of the construct (pBKLD) was performed using Big Dye Termination Kit (Perkin Elmer) with the primers KLDF, J2KLSEQ1 and J2KLSEQ2.

Expression of Kinase-like Domain in *E. coli.*

Recombinant *E. coli* bearing pBKLD were induced for 4 hours with Serakinase at a final concentration of 0.2% as described in the pBAD Protocols book (Invitrogen). Periplasmic Cellular fractions were prepared as recommended in the Invitrogen pBAD Protocols book. Shock Solutions #1 and #2 were then pooled, protease inhibitors added and the KLD domain purified as outlined below.

Dot Blotting using anti-C-Term His Antibody (Invitrogen) was then performed to confirm the presence of expressed KLD domain.

Assays

Cell Based Assay

The murine hematopoietic cell line Ba/F3 was grown in the presence of IL-3. Peptides (PSL$_{short}$ PAEFMRMI (SEQ ID NO:15) and PSL$_{Control}$ SPSKFRMPEAMIGND (SEQ ID NO:16)) were added at concentrations ranging from 1 µM to 100 µM in phosphate buffered saline. Cell number after three days was measured by an MTT assay.

KLD Binding Assay

For fluorescence polarization assays 1-5 µg of purified KLD was incubated in 50 mM HEPES, pH 7.5, 12.5 mM NaCl, 1 mM MgCl$_2$, in the presence or absence of 1 mM ATP. Peptide JL1 (FITC-βAla-YIEKSKSPPAEFM-NH$_2$) (SEQ ID NO:17) was added to a concentration of InM and non-fluoresceinated peptide competitors JLC and JLD were added at 10 or 100 fold molar excess. Fluorescence polarization was measured using a BMG POLARstar.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Blom, N., Gammeltoft, S., and Brunak, S. (1999) Sequence- and Structure-Based Prediction of Eukaryotic Protein Phosphorylation Sites. *Journal of Molecular Biology* 294 1351-1362

Checovich, W. J., Bolger, R. E. and Burke, T. (1995) Fluorescence Polarisation—A new tool for cell and molecular biology. *Nature* 375 254-265

Sadowski H B, Stone J C, Pawson T. (1986) A noncatalytic domain conserved among cytoplasmic protein-tyrosine kinases modifies the kinase function and transforming activity of Fujinami sarcoma virus P130$^{gag-fps}$. *Mol Cell Biol* 6 4396-408.

Hanks S K, Quinn A M, Hunter T. (1988) The protein kinase family: conserved features and deduced phylogeny of the catalytic domains. *Science* 241 42-52.

Hanks S K, Quinn A M. (1991) Protein kinase catalytic domain sequence database: identification of conserved features of primary structure and classification of family members. *Methods Enzymol.* 200 38-62

Harpur A G, Andres A C, Ziemiecki A, Aston R. R. and Wilks, A. F., (1992) JAK2, a third member of the JAK family of protein tyrosine kinases. *Oncogene;* 7 1347-53.

Kozma S C, Redmond S M S, Xiao-Chang F, et al. (1988) Activation of the receptor kinase domain of the trk oncogene by recombination with two different cellular sequences. *EMBO* 7 147-54.

Hubbard S R, Wei L, Ellis L, et al. (1994) Crystal structure of the tyrosine kinase domain of the human insulin receptor. *Nature* 372 746-54.

Overduin M, Rios C B, Mayer B J, et al. (1992) Three-dimensional solution structure of the src homology domain of c-abl. *Cell* 70 697-704.

Schindler T, Bornmann W, Pellicena P, Miller W T, Clarkson B, Kuriyan J (2000) Structural mechanism for STI-571 inhibition of abelson tyrosine kinase. *Science* 289 1938-42

Verderame M F, Varmus H E (1994) Highly conserved amino acids in the SH2 and catalytic domains of v-src are altered in naturally occurring, transformation-defective alleles. *Oncogene* 9 175-82.

Wilks A F, Harpur A G, Kurban R R, Ralph S J, Zurcher G, Ziemiecki A (1991) Two novel protein-tyrosine kinases, each with a second phosphotransferase-related catalytic domain, define a new class of protein kinase. *Mol Cell Biol.* 11 2057-65.

Wilks A F, Kurban R R. (1988) Isolation and structural analysis of murine c-fes cDNA clones. *Oncogene* 3 289-94.

The invention claimed is:

1. A peptide which is capable of inhibiting kinase activity of Janus kinase (JAK), the peptide consisting of the amino acid sequence:

X1-X2-X3-X4-X5-X6-X7-X8    (SEQ ID NO: 52)

wherein:
X1 is proline or glycine;
X2 is alanine, valine, leucine or isoleucine;
X3 is glutamate or aspartate;
X4 is phenylalanine or tyrosine;
X5 is leucine or methionine or isoleucine;
X6 is arginine or lysine;
X7 is methionine or leucine or isoleucine; and
X8 is isoleucine or leucine or methionine.

2. The peptide of claim 1 wherein X1 is proline, X2 is alanine, X3 is glutamate, X4 is phenylalanine, X5 is methionine, X6 is arginine, X7 is methionine and X8 is isoleucine.

3. The peptide of claim 1 wherein X4 is phenylalanine.

4. The peptide of claim 1 wherein X7 is methionine.

5. The peptide of claim 1 wherein X8 is isoleucine.

6. The peptide of claim 1 wherein the peptide is cyclic.

* * * * *